(12) United States Patent
Chen et al.

(10) Patent No.: US 10,898,595 B2
(45) Date of Patent: *Jan. 26, 2021

(54) CORE-SATELLITE NANOCOMPOSITES FOR MRI AND PHOTOTHERMAL THERAPY

(71) Applicant: The Regents of the University of Michigan, Ann Arbor, MI (US)

(72) Inventors: Hongwei Chen, Ann Arbor, MI (US); Duxin Sun, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/694,715

(22) Filed: Nov. 25, 2019

(65) Prior Publication Data
US 2020/0164094 A1 May 28, 2020

Related U.S. Application Data

(60) Continuation of application No. 15/972,674, filed on May 7, 2018, now Pat. No. 10,485,886, which is a division of application No. 14/476,408, filed on Sep. 3, 2014, now abandoned.

(60) Provisional application No. 61/873,941, filed on Sep. 5, 2013.

(51) Int. Cl.
| | | |
|---|---|---|
| *A61B 5/05* | (2006.01) | |
| *A61K 49/18* | (2006.01) | |
| *A61K 41/00* | (2020.01) | |
| *G01R 33/56* | (2006.01) | |
| *G01R 33/48* | (2006.01) | |
| *A61N 5/06* | (2006.01) | |
| *A61B 5/00* | (2006.01) | |
| *A61B 5/055* | (2006.01) | |

(52) U.S. Cl.
CPC ...... *A61K 49/1824* (2013.01); *A61K 41/0052* (2013.01); *A61K 49/183* (2013.01); *A61K 49/1833* (2013.01); *A61K 49/1851* (2013.01); *G01R 33/4808* (2013.01); *G01R 33/5601* (2013.01); *A61B 5/0035* (2013.01); *A61B 5/0075* (2013.01); *A61B 5/055* (2013.01); *A61K 49/1827* (2013.01); *A61N 5/062* (2013.01); *A61N 2005/0659* (2013.01)

(58) Field of Classification Search
None
See application file for complete search history.

(56) References Cited

U.S. PATENT DOCUMENTS 10,458,886 B2 11/2019 Chen et al.
2015/0065848 A1 3/2015 Chen et al.

FOREIGN PATENT DOCUMENTS

WO WO 2008/140624 11/2008
WO WO 2015/034918 9/2015

OTHER PUBLICATIONS

Cabral et al., "Accumulation of sub-100 nm polymeric micelles in poorly permeable tumours depends on size," Nat Nanotechnol 2011, 6: 815-823.
Chen et al., "Biocompatible polysiloxane-containing diblock copolymer PEO-b-PgammaMPS for coating magnetic nanoparticles," Acs Appl Mater Inter 2009, 1: 2134-2140.
Chen et al., "Core/shell structured hollow mesoporous nanocapsules: a potential platform for simultaneous cell imaging and anticancer drug delivery," ACS Nano 2010, 4(10): 6001-6013.
Chen et al., "Highly crystallized iron oxide nanoparticles as effective and biodegradable mediators for photothermal cancer therapy," J Mater Chem B 2014, 2: 757-765.
Chen et al., "Gold Nanocages as Photothermal Transducers for Cancer Treatment," Small 2010, 6: 811-817.
Cheng et al., "PEGylated Micelle Nanoparticles Encapsulating a Non-Fluorescent Near-Infrared Organic Dye as a Safe and Highly-Effective Photothermal Agent for In Vivo Cancer Therapy," Adv Funct Mater 2013, 23:5893-5902.
Cherukuri et al., "Targeted hyperthermia using metal nanoparticles," Adv Drug Deliver Rev 2010, 62: 339-345.
Chu et al. "Near-infrared laser light mediated cancer therapy by photothermal effect of Fe3O4 magnetic nanoparticles," Biomaterials 2013, 34: 4078-4088.
De Laurentiis et al., "Treatment of triple negative breast cancer (TNBC): current options and future perspectives," Cancer Treat Rev 2010, 36 Suppl 3:S80-6.
Dong et al., "Facile Synthesis of Monodisperse Superparamagnetic Fe3O4Core@hybrid@Au Shell Nanocomposite for Bimodal Imaging and Photothermal Therapy," Adv Mater 2011; 23: 5392-5397.
Fan et al., "Multifunctional plasmonic shellmagnetic core nanoparticles for targeted diagnostics, isolation, and photothermal destruction of tumor cells," Acs Nano 2012, 6: 1065-1073.
Fernandez-Fernandez et al., "Comparative Study of the Optical and Heat Generation Properties of IR820 and Indocyanine Green," Mol Imaging 2012, 11: 99-113.
Gobin et al., "Near-Infrared-Resonant Gold/Gold Sulfide Nanoparticles as a Photothermal Cancer Therapeutic Agent," Small 2010, 6: 745-752.
Gu et al., "Magnetic-field-assisted photothermal therapy of cancer cells using Fe-doped carbon nanoparticles," J Biomed Opt 2012, 17(1).

(Continued)

*Primary Examiner* — Michael G. Hartley
*Assistant Examiner* — Melissa J Perreira
(74) *Attorney, Agent, or Firm* — Casimir Jones, S.C.; Jason R. Bond

(57) ABSTRACT

The present invention provides methods, compositions, systems, and kits comprising core-satellite nanocomposites useful for photothermal and/or MRI applications (e.g., tumor treatment and/or imaging). In certain embodiments, the core-satellite nanocomposites comprise: i) a core nanoparticle complex comprising a biocompatible coating surrounding a nanoparticle core, and ii) at least one satellite component attached to, or absorbed to, the biocompatible coating. In some embodiments, the nanoparticle core and satellite component are composed of near-infrared photothermal agent material and/or MRI contrast agent material. In further embodiments, the satellite component is additionally or alternatively composed of near-infrared optical dye material.

5 Claims, 28 Drawing Sheets

(56) References Cited

OTHER PUBLICATIONS

Habash et al., "Thermal therapy, part 1: an introduction to thermal therapy," Crit Rev Biomed Eng 2006, 34: 459-489.
Hirsch et al., "Nanoshell-mediated near-infrared thermal therapy of tumors under magnetic resonance guidance," P Natl Acad Sci USA 2003, 100: 13549-13554.
"A Pilot Study of AuroLase(tm) Therapy in Patients With Refractory and/or Recurrent Tumors of the Head and Neck," Nanospectra Biosciences, Inc. https://clinicaltrials.gov/show/nct00848042:.
"A Pilot Study of AuroLase Therapy in Subjects With Primary and/or Metastatic Lung Tumors," Nanospectra Biosciences, Inc. https://clinicaltrials.gov/show/nct01679470:.
"Aurolase Therapy," Nanospectra Biosciences, Inc. http://www.nanospectra.com/clinicians/aurolasetherapy.html.
Hui et al., "Large-Scale Fe 3O 4 Nanoparticles Soluble in Water Synthesized by a Facile Method," J Phys Chem C 2008, 112:11336-9.
Huang et al., "Cancer cell imaging and photothermal therapy in the near-infrared region by using gold nanorods," J Am Chem Soc 2006, 128: 2115-2120.
Ji et al., "Bifunctional gold nanoshells with a superparamagnetic iron oxide-silica core suitable for both MR imaging and photothermal therapy," J Phys Chem C 2007, 111: 6245-6251.
Kamei et al., "Direct cell entry of gold/iron-oxide magnetic nanoparticles in adenovirus mediated gene delivery." Biomaterials. Mar. 2009;30(9):1809-14.
Ke et al., "Gold-Nanoshelled Microcapsules: A Theranostic Agent for Ultrasound Contrast Imaging and Photothermal Therapy," Angew Chem Int Edit 2011, 50: 3017-3021.
Kennedy et al., "A New Era for Cancer Treatment: Gold-Nanoparticle-Mediated Thermal Therapies," Small 2011, 7: 169-183.
Kuo et al., "Gold Nanorods in Photodynamic Therapy, as Hyperthermia Agents, and in Near-Infrared Optical Imaging," Angew Chem Int Edit 2010, 49: 2711-2715.
Link et al., "How does a gold nanorod melt?" J Phys Chem B 2000, 104: 7867-7870.
Liu et al., "Optimization of surface chemistry on single-walled carbon nanotubes for in vivo photothermal ablation of tumors," Biomaterials 2011, 32: 144-151.
Ma et al., "Indocyanine green loaded SPIO nanoparticles with phospholipid-PEG coating for dual-modal imaging and photothermal therapy," Biomaterials 2013, 34: 7706-7714.
Melancon et al., "Targeted multifunctional goldbased nanoshells for magnetic resonance-guided laser ablation of head and neck cancer," Biomaterials 2011, 32: 7600-7608.
Melancon et al., "Cancer Theranostics with Near-Infrared Light-Activatable Multimodal Nanoparticles," Accounts Chem Res 2011, 44: 947-956.
Park et al., "Ultra-large-scale syntheses of monodisperse nanocrystals." Nat Mater. Dec. 2004;3(12):891-5.
Seino et al., Magnetic Composite Nanoparticle of Au/$\gamma$-Fe$_2$O$_3$ Synthesized by Gamma-Ray Irradiation. Chem Letters May 8, 2003;32(8):690-1.
Stewart et al., *World Cancer Report 2014*, World Health Organization, 2014.
Strekowski et al., "Synthesis of water-soluble nearinfrared cyanine dyes functionalized with [(succinimido)oxy]carbonyl group," J Heterocyclic Chem 2003, 40: 913-916.
Sun et al. "Monodisperse MFe$_2$O$_4$ (M=Fe, Co, Mn) Nanoparticles," JACS 2004, 126:273-279.
Sun et al., "Targeted Cancer Therapy by Immunoconjugated Gold-Gold Sulfide Nanoparticles Using Protein G as a Cofactor," Ann Biomed Eng 2012, 40: 2131-2139.
Tang et al., "Synthesis and Biological Response of Size-Specific, Monodisperse Drug-Silica Nanoconjugates," ACS Nano 2012, 6: 3954-3966.
Tian et al., "Hydrophilic Flower-Like CuS Superstructures as an Efficient 980 nm Laser-Driven Photothermal Agent for Ablation of Cancer Cells," Adv Mater 2011, 23: 3542-3547.
Wang et al., "Iron Oxide @ Polypyrrole Nanoparticles as a Multifunctional Drug Carrier for Remotely Controlled Cancer Therapy with Synergistic Antitumor Effect," ACS Nano 2013, 7: 6782-6795.
Wu et al., "Magnetic iron oxide nanoparticles: synthesis and surface functionalization strategies." Nanoscale Res Lett. Oct. 2, 2008;3(11):397-415.
Xiao et al., "A core/satellite multifunctional nanotheranostic for in vivo imaging and tumor eradication by radiation/photothermal synergistic therapy," J Am Chem Soc 2013, 135(35): 13041-13048.
Xu et al., "Magnetic core/shell Fe3O4/Au and Fe3O4/Au/Ag nanoparticles with tunable plasmonic properties," J Am Chem Soc 2007, 129(28): 8698-8699.
Yang et al., "Multimodal Imaging Guided Photothermal Therapy using Functionalized Graphene Nanosheets Anchored with Magnetic Nanoparticles," Adv Mater 2012, 24: 1868-1872.
Yang et al., "Nano-graphene in biomedicine: theranostic applications," Chem Soc Rev 2013, 42: 530-547.
Yavuz et al., "Gold nanocages covered by smart polymers for controlled release with near-infrared light," Nat Mater 2009, 8: 935-939.
Yu et al., "Synthesis of monodisperse iron oxide nanocrystals by thermal decomposition of iron carboxylate salts," Chem Commun 2004, 2306-2307.
Yue et al., "IR-780 dye loaded tumor targeting theranostic nanoparticles for NIR imaging and photothermal therapy," Biomaterials 2013, 34: 6853-6861.
Zhang et al., "Influence of anchoring ligands and particle size on the colloidal stability and in vivo biodistribution of polyethylene glycol-coated gold nanoparticles in tumor-xenografted mice," Biomaterials 2009, 30: 1928-1936.
Zhang et al., "Tailored Synthesis of Superparamagnetic Gold Nanoshells with Tunable Optical Properties," Adv Mater 2010, 22:1905-1909.
Zhang et al., "Nanopod Formation through Gold Nanoparticle Templated and Catalyzed Cross-linking of Polymers Bearing Pendant Propargyl Ethers," J Am Chem Soc 2010, 132: 15151-15153.
Zheng et al., "Indocyanine green-loaded biodegradable tumor targeting nanoprobes for in vitro and in vivo imaging," Biomaterials 2012, 33: 5603-5609.
Zheng et al., "Enhanced Tumor Treatment Using Biofunctional Indocyanine Green-Containing Nanostructure by Intratumoral or Intravenous Injection," Mol Pharmaceut 2012, 9: 514-522.
Zhou et al., "Luminescent gold nanoparticles with efficient renal clearance," Angew Chem Int Ed Engl 2011, 50: 3168-3172.
International Search Report and Written Opinion for PCT/US2014/053892, dated Dec. 8, 2014, 14 pages.

US 10,898,595 B2

CORE-SATELLITE NANOCOMPOSITES FOR MRI AND PHOTOTHERMAL THERAPY

The present application is a continuation of U.S. patent application Ser. No. 15/972,674, filed May 7, 2018, which is a divisional of U.S. patent application Ser. No. 14/476,408, filed Sep. 3, 2014, now U.S. Pat. No. 10,485,886, which claims priority to U.S. Provisional application Ser. No. 61/873,941, filed Sep. 5, 2013, each of which is herein incorporated by reference in its entirety.

FIELD OF THE INVENTION

The present invention provides methods, compositions, systems, and kits comprising core-satellite nanocomposites useful for photothermal and/or MRI applications (e.g., tumor treatment and/or imaging). In certain embodiments, the core-satellite nanocomposites comprise: i) a core nanoparticle complex comprising a biocompatible coating surrounding a nanoparticle core, and ii) at least one satellite component attached to, or absorbed to, the biocompatible coating. In some embodiments, the nanoparticle core and satellite component are composed of near-infrared photothermal agent material and/or MRI contrast agent material. In further embodiments, the satellite component is additionally or alternatively composed of near-infrared optical dye material.

BACKGROUND

Photothermal therapy (PTT) using near-infrared-resonant nanomaterials has gained great attention in recent years (1-4). To date, most photothermal conducting agents have been based on various gold (Au) nanostructures, including nanoshells, nanorods, nanocages, and gold sulfide nanoparticles (5, 6, 7-10). Among them silica-core Au nanoshell have advanced into clinical trials under the brand name Aurolase (11-13). Multifunctional probes with both therapeutic functions and imaging capabilities (e.g., magnetic resonance imaging) have also developed (14-18). However, various challenges still exist. For example, the size of Au nanoshells is too big to effectively target to tumor tissue (15). So intratumor injection of nanoparticles has to be used (5). And gold nanorods may be destroyed after laser irradiation due to the "melting effect" (19). While for the development of multifunctional probes, multiple steps are needed to prepare these nanoparticles.

SUMMARY OF THE INVENTION

The present invention provides methods, compositions, systems, and kits comprising core-satellite nanocomposites useful for photothermal and/or MRI applications (e.g., tumor treatment and/or imaging). In certain embodiments, the core-satellite nanocomposites comprise: i) a core nanoparticle complex comprising a biocompatible coating surrounding a nanoparticle core, and ii) at least one satellite component attached to, or absorbed to, the biocompatible coating. In some embodiments, the nanoparticle core and satellite component are composed of near-infrared photothermal agent material and/or MRI contrast agent material. In further embodiments, the satellite component is additionally or alternatively composed of near-infrared optical dye material.

In some embodiments, the present invention provides methods of treating and/or imaging at least one tumor (e.g., 1 tumor, 2 tumors, 3 tumors, etc.) in a subject comprising: a) administering to a subject a composition comprising core-satellite nanocomposites (e.g., a plurality of nanocomposites or at least 100,000 or at least 1 million, or at least 10 million, etc.), wherein the subject comprises at least one tumor, wherein the core-satellite nanocomposites individually comprise: i) a core nanoparticle complex comprising a biocompatible coating surrounding a nanoparticle core, wherein the nanoparticle core comprises a first type of material selected from: near-infrared photothermal agent material and MRI contrast agent material, and ii) at least one satellite component attached to, or absorbed to, the biocompatible coating, wherein the at least one satellite component comprises a second type of material selected from: the near-infrared photothermal agent material, the MRI contrast agent material, and near-infrared optical dye material, and wherein the treating is under conditions such that at least a portion of the core-satellite nanocomposites infiltrate the at least one tumor; and b) subjecting the subject to photothermal therapy and/or imaging, wherein the photothermal therapy: A) comprises the use of a treatment device that emits electromagnetic radiation, and B) causes the at least one tumor to be reduced in size or become undetectable; and wherein the imaging: A) comprises the use of an imaging device configured for MRI/NMR detection and/or optical detection, and B) causes the at least one tumor to be visualized ex-vivo (e.g., on a computer screen, etc.).

In certain embodiments, the present invention provides methods of treating and/or imaging cancer cells in a subject comprising: a) administering to a subject a composition comprising core-satellite nanocomposites, wherein the subject comprises a plurality of cancer cells, wherein the core-satellite nanocomposites individually comprise: i) a core nanoparticle complex comprising a biocompatible coating surrounding a nanoparticle core, wherein the nanoparticle core comprises a first type of material selected from: near-infrared photothermal agent material and MRI contrast agent material, and ii) at least one satellite component attached to, or absorbed to, the biocompatible coating, wherein the at least one satellite component comprises a second type of material selected from: the near-infrared photothermal agent material, the MRI contrast agent material, and near-infrared optical dye material, and wherein the administering generates a plurality of core-satellite nanocomposite-impregnated cancer cells in the subject; and b) subjecting the subject to photothermal therapy and/or imaging, wherein the photothermal therapy: A) comprises the use of a treatment device that emits electromagnetic radiation, and B) causes at least a portion of the core-satellite nanocomposite-impregnated cancer cells to be damaged or killed; and wherein the imaging: A) comprises the use of an imaging device configured for MRI/NMR detection and/or optical detection, and B) causes at least a portion of the core-satellite nanocomposite-impregnated cancer cells to be visualized ex-vivo.

In certain embodiments, the first and second types of material are different or are the same (e.g., same material, but the core nanoparticle complex and the satellite component are different sizes). In further embodiments, the photothermal therapy causes the at least one tumor to be reduced in size at least 50% (e.g., three weeks after treatment). In other embodiments, the administering comprises administering the composition to the subject intravenously. In further embodiments, the treatment device emits electromagnetic radiation with a wavelength between about 650 and 1000 nm, or 865 nm and 1000 nm. In additional embodiments, the treatment device comprises a laser and/or LED. In other embodiments, the subjecting the subject to photothermal therapy is no more than 5-15 minutes per day (e.g., for 1 days . . . 5 days . . . or 10 days or more).

In some embodiments, the treatment device further comprises a visible light source, wherein the visible light source allows a user to determine where the electromagnetic radiation is contacting the subject. In other embodiments, the treatment device further comprises a component that reveals the temperature of the subject's skin. In particular embodiments, the treatment device further comprises a thermal imaging component. In certain embodiments, the subject is a human, domesticated animal, cat, dog, or horse. In further embodiments, the subject is treated with a dosage of the core-satellite nanocomposites of 10-40 mg/Kg of the subject's body weight (e.g., 10 . . . 21 . . . 37 . . . or 40 mg/Kg). In additional embodiments, the at least one tumor is selected from the group consisting of: a breast tumor, a skin tumor, a kidney tumor, a lymph node tumor, a brain tumor, a liver tumor, a pancreatic tumor, a colon tumor, a lung tumor, an esophagus tumor, and prostate tumor.

In additional embodiments, the methods further comprise a step after step a), or after steps a) and b), of treating the subject in a manner that causes the at least one satellite component to disassociate from the core nanoparticle complex (e.g., thereby allowing the at least one satellite component to penetrate deeper into the at least one tumor than possible with the core-satellite nanocomposites). In further embodiments, treating the subject comprises exposing the subject to a laser, heat, or a change in pH.

In some embodiments, the present invention provides compositions comprising a plurality of core-satellite nanocomposites, wherein the core-satellite nanocomposites individually comprise: a) a core nanoparticle complex comprising a biocompatible coating surrounding a nanoparticle core, wherein the nanoparticle core comprises a first type of material selected from: near-infrared photothermal agent material and MRI contrast agent material, and b) at least one satellite component attached to, or absorbed to, the biocompatible coating, wherein the at least one satellite component is smaller than the core nanoparticle complex and comprises a second type of material selected from: the near-infrared photothermal agent material, the MRI contrast agent material, and near-infrared optical dye material. In particular embodiments, the compositions comprising a physiologically compatible aqueous solution.

In certain embodiments, the present invention provides systems comprising: a) a composition comprising core-satellite nanocomposites, wherein the core-satellite nanocomposites individually comprise: i) a core nanoparticle complex comprising a biocompatible coating surrounding a nanoparticle core, wherein the nanoparticle core comprises a first type of material selected from: near-infrared photothermal agent material and MRI contrast agent material, and ii) at least one satellite component attached to, or absorbed to, the biocompatible coating, wherein the at least one satellite component comprises a second type of material selected from: the near-infrared photothermal agent material, the MRI contrast agent material, and near-infrared optical dye material; and b) a device component selected from: i) a treatment device that emits electromagnetic radiation (for photothermal therapy), and ii) an imaging device configured for MRI/NMR detection and/or optical detection.

In certain embodiments, the device component comprises the treatment device. In other embodiments, the device component comprises the imaging device. In further embodiments, the treatment device is configured to emit electromagnetic radiation at least in the wavelengths between about 650 nm and 1000 nm.

In further embodiments, the first type of material is selected from the group consisting of: $Fe_3O_4$, silicon, gold, copper, and carbon. In particular embodiments, the first type of material comprises $Fe_3O_4$. In additional embodiments, the $Fe_3O_4$ is highly crystallized and has an X-ray diffraction (XRD) pattern where the brightest diffraction ring is from the 440 plane. In further embodiments, the $Fe_3O_4$ has a preferred lattice orientation along the 400 and 440 XRD diffraction planes. In other embodiments, the second type of material is selected from the group consisting of: gold, gold sulfide ($Au_2S$), copper, copper sulfide ($Cu_2S$), carbon, carbon nanotubes, and graphene. In certain embodiments, the second type of material comprises gold sulfide ($Au_2S$). In other embodiments, the near-infrared optical dye material is selected from the group consisting of: IR820, ICG, and 5, aminolevulinic acid (5-ALA).

The present invention is not limited by the shape of the core or the satellite particle. Examples of shapes include, but are not limited to, spherical, cubic, rod shaped, disc shaped, etc.

In some embodiments, the at least one satellite component has a size between 0.5 nm and 50 nm in diameter (e.g., 0.5 . . . 1.5 . . . 10 . . . 23 . . . 32 . . . 46 . . . and 50 nm). In further embodiments, the at least one satellite component is smaller than (or the same size as) the core nanoparticle complex. In other embodiments, the at least one satellite component is larger than the core nanoparticle complex. In further embodiments, the at least one satellite component has a size between 2 nm and 7 nm in diameter (e.g., about 5 nm). In further embodiments, the nanoparticle core has a size between 4 and 60 nm in diameter. In additional embodiments, the nanoparticle core has a size between 10 and 20 nm in diameter.

In further embodiments, the core-satellite nanocomposites are present in the composition at a concentration of between 1.0 and 5.0 mg/mL (e.g., 1.0 . . . 3.3 . . . and 5.0 mg/ml). In other embodiments, the biocompatible coating comprises a material selected from the group consisting of: human serum albumin (HSA), polyethylene glycol, triblock copolymer, PEO-b-PPO-b-PEO (F121), PEO-b-PVP, glucosylated poly(pentafluorostyrene), chitosan, silica, and gum Arabic, gluconic acid, lactobionic acid, polyacrylic acid, apatite, and Casein. In additional embodiments, the biocompatible coating is functionalized with thiol groups or amine groups. In particular, one can use siloxane molecules like (3-Mercaptopropyl) trimethoxysilane (MPTMS) to produce thiol groups or (3-Aminopropyl)triethoxysilane to produce amine groups on nanoparticle surfaces to functionalize polymer coated nanoparticles.

DESCRIPTION OF THE FIGURES

FIG. 21, Panel B shows MCF-7 spheroid incubated in medium after Prussian Blue Staining as a control image. Higher magnification pictures of MCF-7 spheroids treated with IONPs (Panel C) and IONP/Au2S core/satellites nanocomposite (Panel D) after Prussian Blue staining. Iron concentration were kept at 0.1 mg/ml in both groups and iron composition were stained in blue.

DETAILED DESCRIPTION

Figure 1:
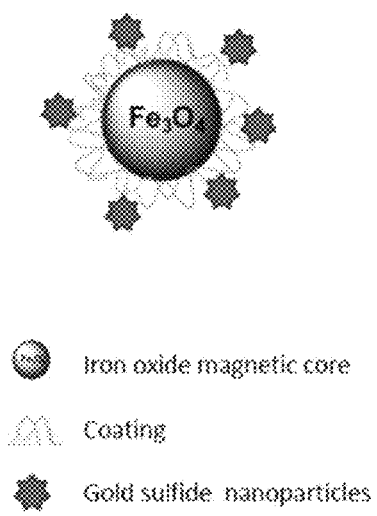
FIG. 1 shows a TEM image of IONP-$Au_2S$ core-satellite nanocomposite, where the magnetic core is 15 nm in diameter and is further attached with multiple $Au_2S$ nanoparticles.
Figure 1:
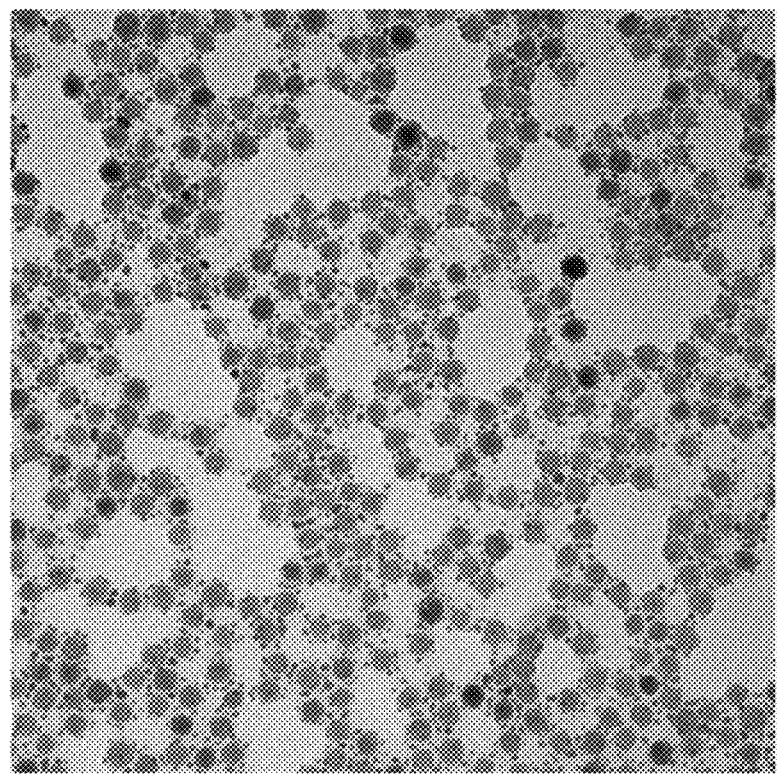

The present invention provides methods, compositions, systems, and kits comprising core-satellite nanocomposites useful for photothermal and/or MRI applications (e.g., tumor treatment and/or imaging). In certain embodiments, the core-satellite nanocomposites comprise: i) a core nanoparticle complex comprising a biocompatible coating surrounding a nanoparticle core, and ii) at least one satellite component attached to, or absorbed to, the biocompatible coating. In some embodiments, the nanoparticle core and satellite component are composed of near-infrared photothermal agent material and/or MRI contrast agent material. In further embodiments, the satellite component is additionally or alternatively composed of near-infrared optical dye material.

In certain embodiments, the core-satellite nanocomposites described herein are used for treating a conditions such as cancer and/or a condition associated with vascular tissue or cells, for example, atherosclerosis. In certain embodiments, the core-satellite nanocomposites are targeted to cells, tissue or other site of interest associated with the condition, will absorb near infrared radiation delivered thereto and, upon becoming heated by the NIR, result in selective thermolysis or ablation or other damage or cell death without damaging untargeted cells or tissues. Devices and methods for delivering radiation of a particular wavelength, such as by, but not limited to, lasers, to a targeted site are well-known and standard in the art. In some embodiments, the core-satellite nanocomposites are used as MR contrast agents, with or without subsequent photothermal therapy.

The present invention is not limited by the type of near-infrared photothermal agent material that is employed. Examples of such agents include, but are not limited to, $Fe_3O_4$, gold, silica, CuTe, $MoS_2$, cobalt, nickel, palladium, platinum, copper, silver, or aluminum.

The present invention is not limited by the type of MRI contrast agent material that is employed. Examples of such agents include, but are not limited to, gadolinium, gold, iron oxide, gold sulfide ($Au_2S$), copper sulfide ($Cu_2S$), carbon nanotubes, graphene, iron platinum, manganese, and other MRI contrast agents known in the art.

The present invention is not limited by the type of near-infrared optical material that is employed. Examples of such agents include, but are not limited to, IR820, ICG, 5, aminolevulinic acid (5-ALA), Cy5, Alexa Fluor 700, DY730, Alexa Fluor 750, and DY780.

EXAMPLES

Example 1

Core-Satellite Nanocomposites for MRI and/or Photothermal Therapy

This Examples describes the design of core-satellite hybrid nanocomposites with highly crystalized iron oxide nanoparticles (IONPs) as the core and multiple gold sulfide ($Au_2S$) nanoparticles as satellites attached on the surface polymer coated IONP. In this formulation, the multiple satellites ($Au_2S$) could be used for photothermal therapy, while the IONP core could be used as both photothermal mediator and magnetic resonance imaging (MRI) contrast agent. These nanocomposites could also be used in MRI guidable photothermal therapy. This core-satellite nanocomposite has obvious absorption in near infrared range and the absorption peak could be adjusted. The nanocomposites exhibit an obvious temperature rise without any quenching under laser irradiation in comparison to the water control. These nanocomposites benefit benefited from an anti-biofouling polymer coating and can effectively accumulate to tumor sites through enhanced permeability and retention. Enhanced by the nanocomposites around a tumor site, tumor cells are killed greatly and the tumor tissue is damaged a lot after laser irradiation.

Materials and Methods
Materials.

Iron oxide (III) (FeO(OH), hydrated, catalyst grade, 30-50 mesh), oleic acid (technical grade, 90%), 1-octadecene (technical grade, 90%), anhydrous tetrahydrofuran (THF, 99.8%), ammonium iron (II) sulfate hexahydrate (Fe$(NH_4)_2(SO_4)_2 \cdot 6H_2O$, ACS reagent, 99%), o-phenanthroline monohydrate (ACS reagent, 99%), hydroquinone (ACS reagent, 99%), sodium sulfide, sodium thiosulfide, chloroauric acid, (3-Mercaptopropyl)trimethoxysilane were purchased from Aldrich.

Synthesis of IONPs.

IONPs (15 nm in diameter) were synthesized in organic solvent by thermal decomposition as reported previously with a slight modification (20). Briefly, a mixture of 0.890 g FeO(OH), 19.8 g oleic acid and 25.0 g 1-octadecene in a three-neck flask was heated under stirring to 200° C. under $N_2$, 30 minutes later the temperature was set at 220° C. for 1 h, then the temperature was increased gradually to 310° C. (20° C./5 minutes) and kept at this temperature for 1 h. The solution became black when the temperature was increased to 320° C. and kept at this temperature for 1 h. After the reaction was completed, the reaction mixture was cooled and the nanocrystals were precipitated by adding chloroform and acetone.

Testing IONPs—

Figure 13:
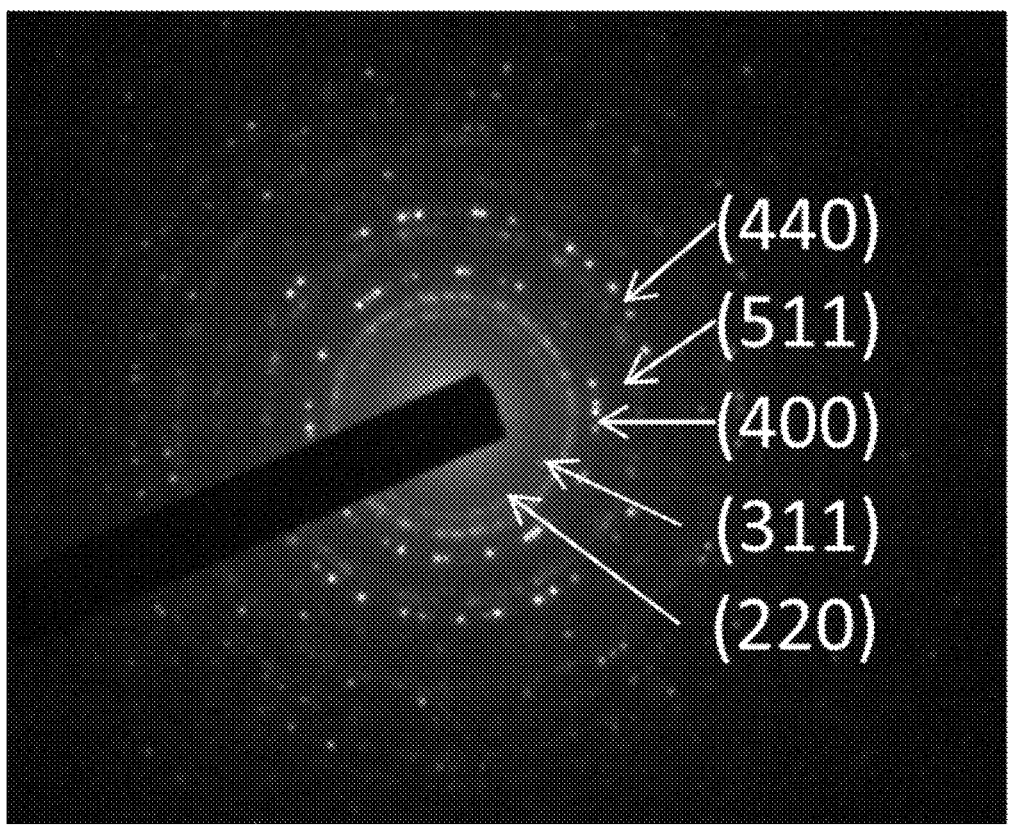
FIG. 13 shows an electron diffraction of IONPs as prepared in Example 1.

The IONPs were tested and it was found that the brightest diffraction ring was 440 (FIG. 13).

Coating of IONPs with Polysiloxane-Containing Diblock Copolymer.

Diblock copolymer (PEO-b-P$_y$MPS) was synthesized by the reversible addition of fragmentation chain transfer (RAFT) polymerization as previously reported (21). The method for coating single core nanocrystals was reported previously with a slight modification (21; herein incorporated by reference). Briefly, the purified nanocrystals (100.0 mg) were dispersed in 10 mL of anhydrous THF and then mixed with the newly synthesized copolymer (1.00 g) in 10 mL of anhydrous THF. After being aged for four days, the mixture was added dropwise into 100 mL of water with gentle magnetic stirring. THF in the solution was removed by dialysis using deionized water. The resultant solution was then purified by using a magnetic separator (Frantz laboratory). This wash-resuspend step was repeated three times. The average hydrodynamic diameter was measured using a dynamic light scattering instrument (Malvern Zeta Sizer Nano S-90). The magnetic nanocrystals were viewed by transmission electron microscopy (TEM) (Philips CM-100 60 kV), with the polymer coating made visible by negative staining with $OsO_4$. High-resolution TEM was taken on a JEOL 3011 microscope. UV-vis-NIR spectra were recorded in a BioTek micro-plate reader (Synergy 2) using 200 µL of aqueous solution.

Synthesis of $Au_2S$ nanoparticles.

$Au_2S$ nanoparticles were made by using sodium sulfide ($Na_2S$) or sodium thiosulfide ($Na_2S_2O_3$) as the reducing reagent as reported before (22 and 23; herein incorporated by reference). Gold in the form of chloroauric acid ($HAuCl_4$) was prepared to a concentration of 100 mM and was diluted to 2 mM when used. $Na_2S$ (1 mM) was prepared, and weas aged in darkness for 40-48 h prior to use. The ratio of $HAuCl_4$ to $Na_2S$ was varied from 1.0:1.0 up to 1.0:1.4 by volume. Spectra were monitored over time with a UV/Vis spectrophotometer. For using $Na_2S_2O_3$ as the reducing reagent, gold in the form of chloroauric acid was prepared to a concentration of 100 mM and was diluted to 2 mM when use. Sodium thiosulfide (3 mM) was prepared. The ratio of sodium thiosulfide to chloroauric acid was varied from 2.5:1 up to 3.5:1 by volume.

Make IONP/Au₂S Core/Satellite Nanocomposite.

To make core-satellite nanocomposites, the IONPs were modified with (3-Mercaptopropyl)trimethoxysilane (MPTMS) to produce surface thiol groups. 2 mL of 1.8 mg/mL water soluble IONP solution was added with 80 μL MPTMS solution (80 μL MPTMS in 800 μL DMSO). The reaction was carried out at room temperature with gentle stirring for two days. After this, freshly made Au₂S nanoparticle solution (11 mL) was mixed together for overnight. The resultant nanocomposites were purified through magnet. The supernatant was discarded and the concentrated solution was diluted with the same amount of water and this process was repeated three times.

Determination of Iron Concentration Using Spectrophotometry.

10 μL of concentrated nanoparticle solution was diluted with 2 mL of Milli-Q water, followed by adding 200 μL of concentrated HCl solution. After two days, sodium citrate was added to adjust the solution pH to 3.5. Then 2 mL of hydroquinone (10 g/L) and 3 mL of o-phenanthroline (2.5 g in 100 mL of ethanol and 900 mL of water) was added to the solution followed by adjusting to a specific volume using Milli-Q water. Five standard Fe solutions using $Fe(NH_4)_2(SO_4)_2 \cdot 6H_2O$ were also made. To determine the solution concentration of iron, calibration curves were generated by measuring optical absorbance of solutions at 508 nm.

Photothermal Effect of Nanocomposites in Aqueous Solution.

To study the photothermal effect of core-satellite hybrid nanocomposite induced by NIR light, the aqueous solutions (1.0 mL) of the nanocrystals with different Fe concentrations in a cuvette were irradiated using an NIR laser (885 nm, spot size, 5×8 mm², MDL-III-885, OPTO Engine LLC, Midvale, Utah) for 10 minutes. The temperature of the solutions was measured by a digital thermometer.

Xenograft Mouse Model.

All studies involving mice were conducted in accordance with a standard animal protocol approved by the University Committee on the Use and Care of Animals at the University of Michigan. Five week old nude mice were obtained from Charles River Breeding Laboratories. Xenograft formation was generated by direct injection of $5 \times 10^5$ SUM-159 cells, suspended in matrigel, into the exposed no. 4 inguinal mammary pad. Tumor detection was assessed by palpation and once identified measurement of tumor volume was carried out using digital calipers and calculated by volume= $(width)^2 \times length/2$.

In Vivo PTT.

Tumor-bearing nude mouse were intravenously injected with magnetic nanoparticles (20 mg Fe/Kg mouse body weight). 48 h post injection, tumors were irradiated with a diode laser ($\lambda$=885 nm) at a fluence rate of 2.5 W/cm² for 10 minutes. The highest tumor surface temperature was recorded by an infrared camera (FLIR Systems, i7, Boston, Mass.) before and after application of the laser. Mouse injected with PBS and treated with the same laser was used as control.

In Vitro MRI and T2 Relaxivity Measurement.

Magnetic resonance imaging (MRI) studies were carried out by using an MRI scanner at 7.4 T field strength. For T2 measurements, a multiecho fast spin-echo sequence was used to simultaneously collect a series of data points at different echo times (TE=15-90 ms with an increment of 15 ms). The T2 relaxation time of each nanoparticle sample was calculated by fitting the decay curve on a pixel-by-pixel basis by using a nonlinear nonoexponential algorithm $M(TE)=M0 \exp(-TEi/T2)$, where TE is the echo time, M(TE) is the MRI signal intensity at which TE is used.

MRI of Tumor-Bearing Mice Administered with IONP/Au2S Nanocomposite.

Tumor-bearing nude mice were scanned with a wrist coil to collect pre- and post-contrast enhanced MRI data. Images from pre- and post-contrast administration were compared to evaluate the contrast enhancement. Mice were imaged before and 24 h after tail vein injection with as-prepared nanocomposites (20 mg Fe per kg mouse body weight). T2 weighted fast spin-echo sequence was used to obtain T2 relaxometry of the tumor tissue. The averaged signal intensity of whole tumors was calculated manually using ImageJ (U.S. National Institutes of Health, Bethesda, Md., USA) for comparing the signal intensity before and after injection of magnetic nanoparticles.

Biodistribution.

SUM-159 tumor-bearing BALB/c mice were used for this study. Mice (four to five mice in each group) were intravenously injected with HCIONPs (as-prepared polymercoated HCIONPs were the only type used for all in vivo studies in this work) at a dose of 15 mg Fe per kg mouse body weight. Mice in another group were used as a control without any injection. After 48 h, animals were sacrificed. Blood samples were collected by terminal heart puncture and centrifuged for 10 minutes at 5000 rpm to separate the serum. The tissue samples of tumor, liver, spleen, lungs, kidney, heart, brain, stomach, and muscle were collected and weighed. To determine the iron concentrations in the serum or major organs, 200 mL of serum or whole organ tissue samples were digested in 1 mL of nitric acid (2 mL for liver). After filtration (acrodisc syringe filters, PTFE membrane, diameter 13 mm, pore size 0.45 mm), the volumes of solutions were adjusted to 10.0 mL and the iron concentration was analyzed using inductively coupled plasma optical emission spectrometry (ICP-OES) with yttrium as the internal standard.

Histology.

Mice were humanely euthanized by CO2 inhalation two days following a single I.V. bolus dose of nanoparticles. The harvested tissue was formalin-fixed, embedded in paraffin and sectioned. Unstained slides were dewaxed using xylene and rehydrated using graded alcohol. Rehydrated slides were stained with Prussian Blue reagent for visualization of iron content and were counter stained with Nuclear Fast Red to show cellular structure.

MTS Assay.

The MTS assay it is based on tetrazolium compound MTS and an electron coupling reagent (phenazine ethosulfate; PES) reducing into a soluble formazan product. This conversion requires the presence of metabolically active cells, which allow the presence of mitochondrial dehydrogenase enzyme. The formazan product can be measured by UV absorbance at 490 nm, which is directly proportional to the number of live cells in culture and can thus be used for determining the number of viable cells in proliferation or cytoxicity assays. MTS assay was carried out on SUM159 cell line. A 20 μl portion of Cell Titer 96 Aqueous One Solution reagent was added to each well of a cell loaded 96-well plate treated with IONP/Au2S at different concentrations after 24 h post nanoparticle introduction, then plates were incubated in a humidified incubator at 37 C for 1 h, and the absorbance was measured at 490 nm.

Uptake of IONP/AuS Nanocomposite by Monolayer SUM159 Cells.

The breast cancer cell line SUM159 was used to evaluate the particle cell uptake in conjunction with in vivo experiments. SUM159 was maintained as adherent monolayers in a humidified incubator (95% air; 5% CO2) at 37° C. in a Petri dish containing Ham's F-12 (Invitrogen) supplemented with 5% FBS, 5 ug/mL insulin, and 1 ug/mL hydrocortisone. To test the uptake efficiency of IONP/Au2S nanocomposites with different concentrations, cells were seeded into six-well plates and left overnight and treated with different concentrations of as-prepared nanoparticles for 8 h. After exposure to IONP/Au2S nanoparticles, cells were washed with PBS twice and digested in freshly made aqua regia overnight. The aqua regia solutions were transferred to 15 ml centrifuge tubes and the final volumes were adjusted using Milli-Q water. The final iron and gold content was measured using inductively coupled plasma optical emission spectrometry (ICP-OES).

Prussian Blue Staining.

Qualitative assessment was carried out by seeding SUM159 cells into a 8-well glass chamber slide and left overnight. Cells were treated with IONP/Au2S and IONP at the same iron concentration (0.1 mg/ml) for 12 h one day after seeding. After incubation, cells were washed twice with PBS and were fixed with 0.5 mL of 4% paraformaldehyde for an hour. Prussian blue staining was used to determine the presence of iron in the cells. Each well of the chamber slide was filled with 0.5 mL of 5% potassium ferrocyanide (II) trihydrate and 5% HCl solution and incubated for 15 min. After being washed three times with distilled water, cells were counterstained with nuclear fast red solution for 5 min. After consecutive dehydrations with 70% and 100% EtOH, the slide was mounted. The result of Prussian blue staining was assessed by a bright field optical microscope.

MCF-7 Multicellular Spheroid Culture.

MCF-7 Multicelluar Spheroid Culture. MCF-7 spheroids were produced by a well-developed method. In brief, MCF-7 cells were detached from Petri dish, and single cell suspensions (200 μL per well containing 600 cells) were transferred into flat bottomed ulrea-low 96-well plates. Cells were incubated in DMEM supplemented with 10% FBS and 5 ml anti-anti for about 7 days. Culture medium was partially (100 μL) replaced by fresh medium every other day.

TEM Observation of Spheroids and Monolayer of Cells.

In order to evaluate the particle distribution and ultralocalization within the cell spheroids, TEM was carried out. In brief, 7-daycultured spheroids were removed and transferred to a cell strainer and washed twice with PBS. The collected spheroids were fixed overnight at room temperature using 3% glutaraldehyde solution which was followed by secondary fixation with 1% osmium tetraoxide, then serial dehydration in a graded ethanol series. Each spheroid was embedded in Epon resin and polymerized for 24 h at 60° C. Embedded samples were sectioned, stained with uranyl acetate, and examined under an electron microscope (Philips CM-100 transmission electron microscope). For cell monolayers, cells were detached from the dish using a cell scraper. After transferred to a centrifuge tube, cells were processed as described for spheroids. The ultramicrolocalization of IONP/Au2S nanoparticles in the outer and inner cells of the spheroid was evaluated by TEM.

Results

Figure 2:
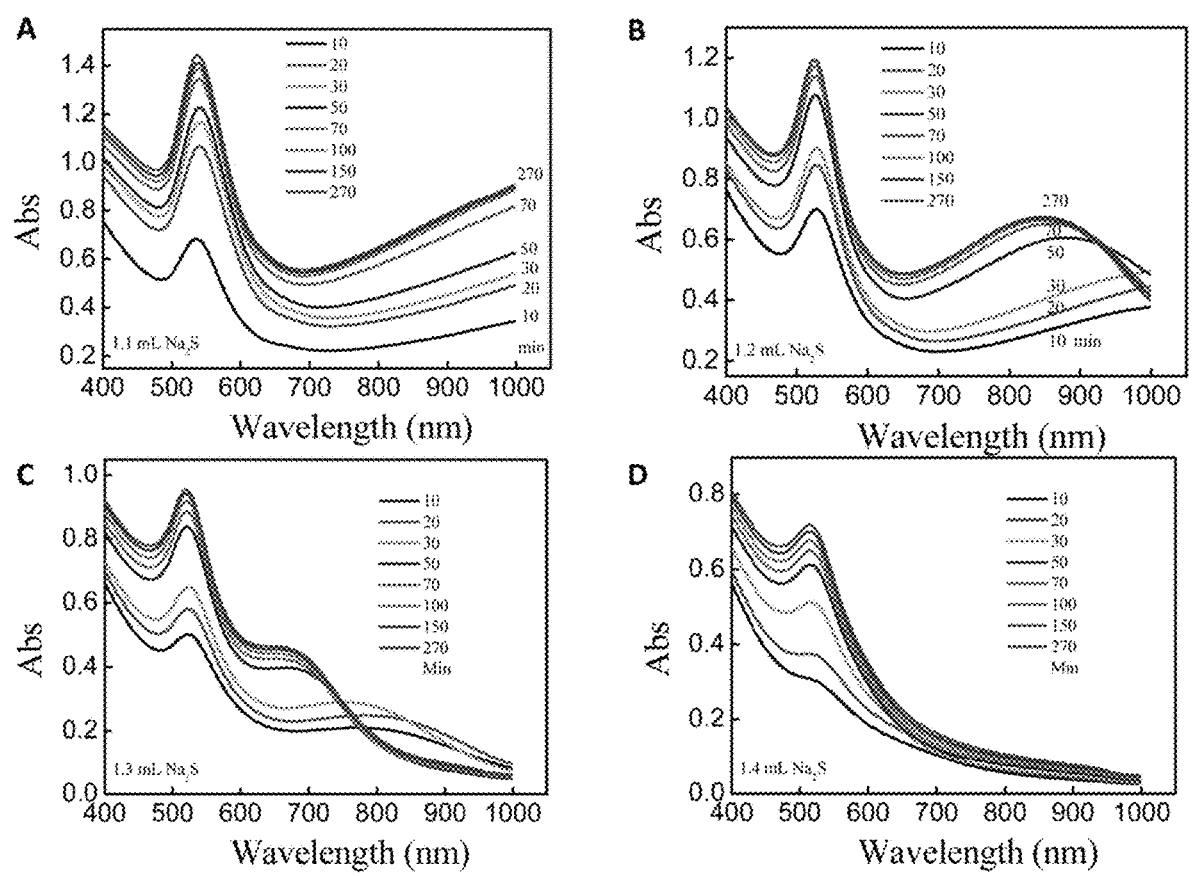
FIG. 2, panels A-D show the optical spectrum of $Au_2S$ nanoparticles with adjustable peak at near infrared range. $Au_2S$ nanoparticles were produced by mixing $HAuCl_4$ (1.0 mL, 2 mM) and serials of volume of $Na_2S$ (1 mM) in water (A: 1.1, B: 1.2, C: 1.3, and D: 1.4 mL). In each figure, data were recorded over time until the curve is unchangeable.
Figure 3:
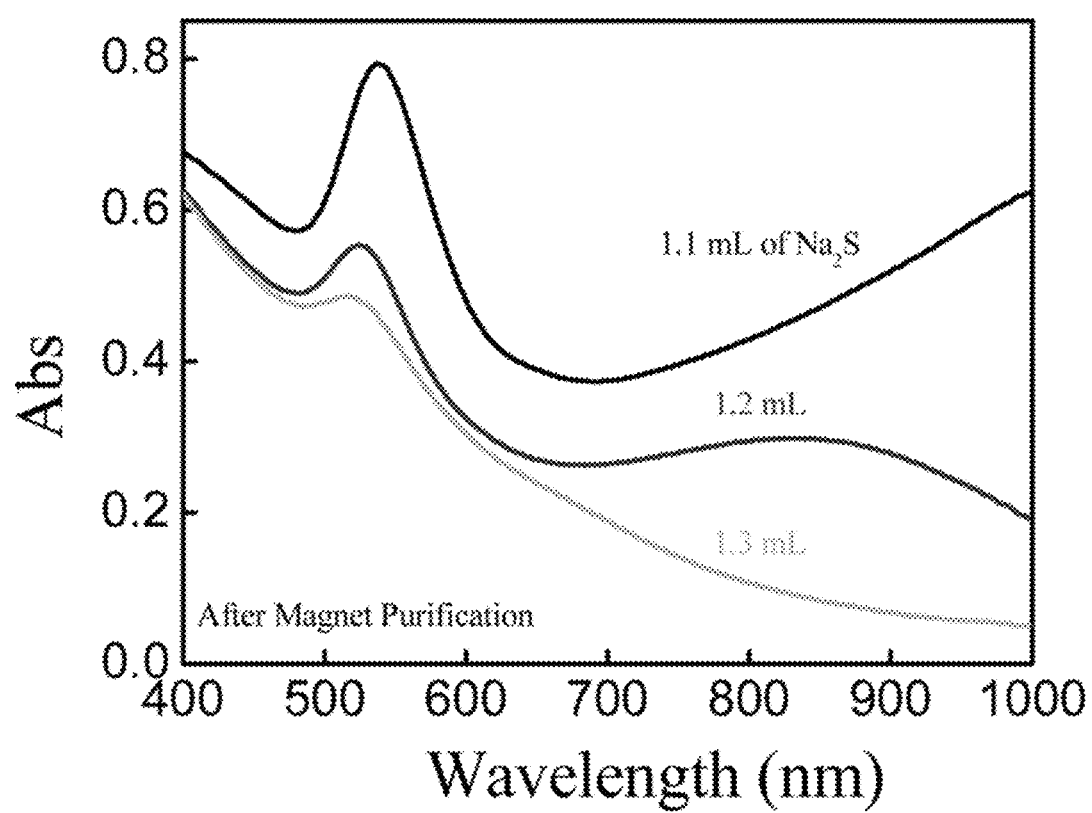
FIG. 3 shows an absorption spectrum of IONP-$Au_2S$ core-satellite nanocomposites, where the infrared absorption is adjustable by controlling the amount of sodium sulfide.
Figure 4:
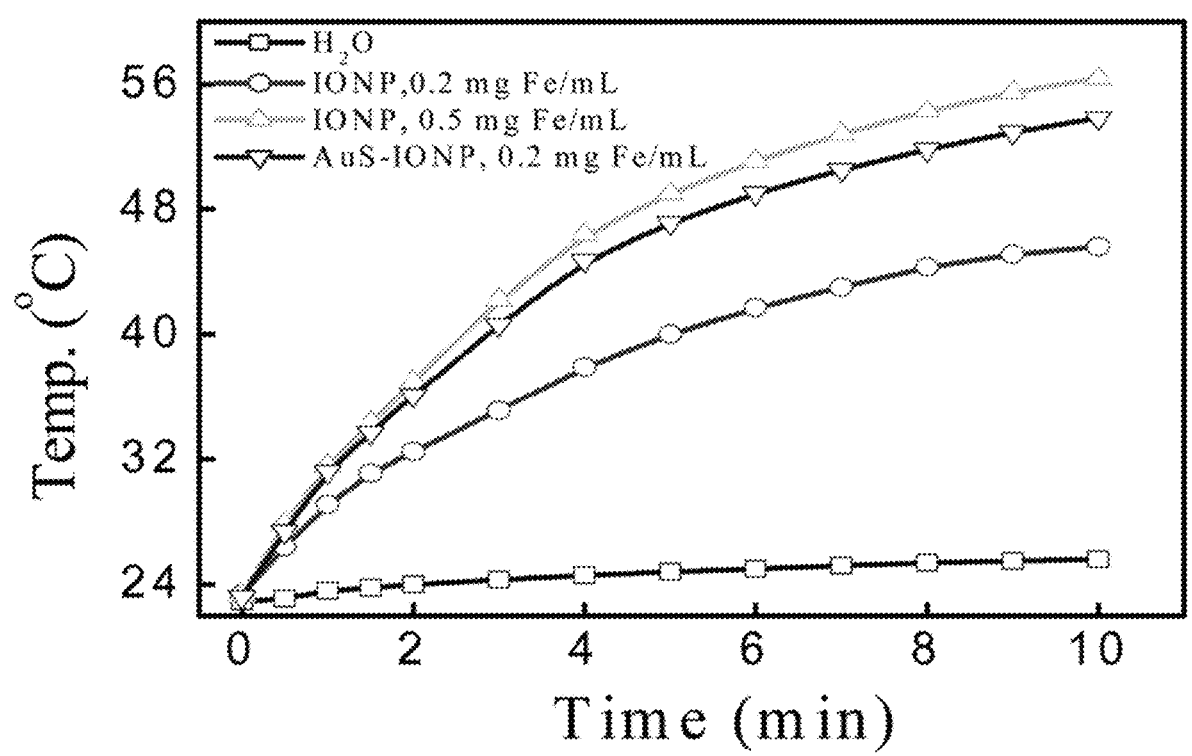
FIG. 4 shows the measured temperature of IONP-Au$_2$S core-satellite nanocomposite and IONPs only after irradiation with a diode laser (λ=885 nm) at a fluence rate of 2.5 W/cm$^2$.
Figure 5:
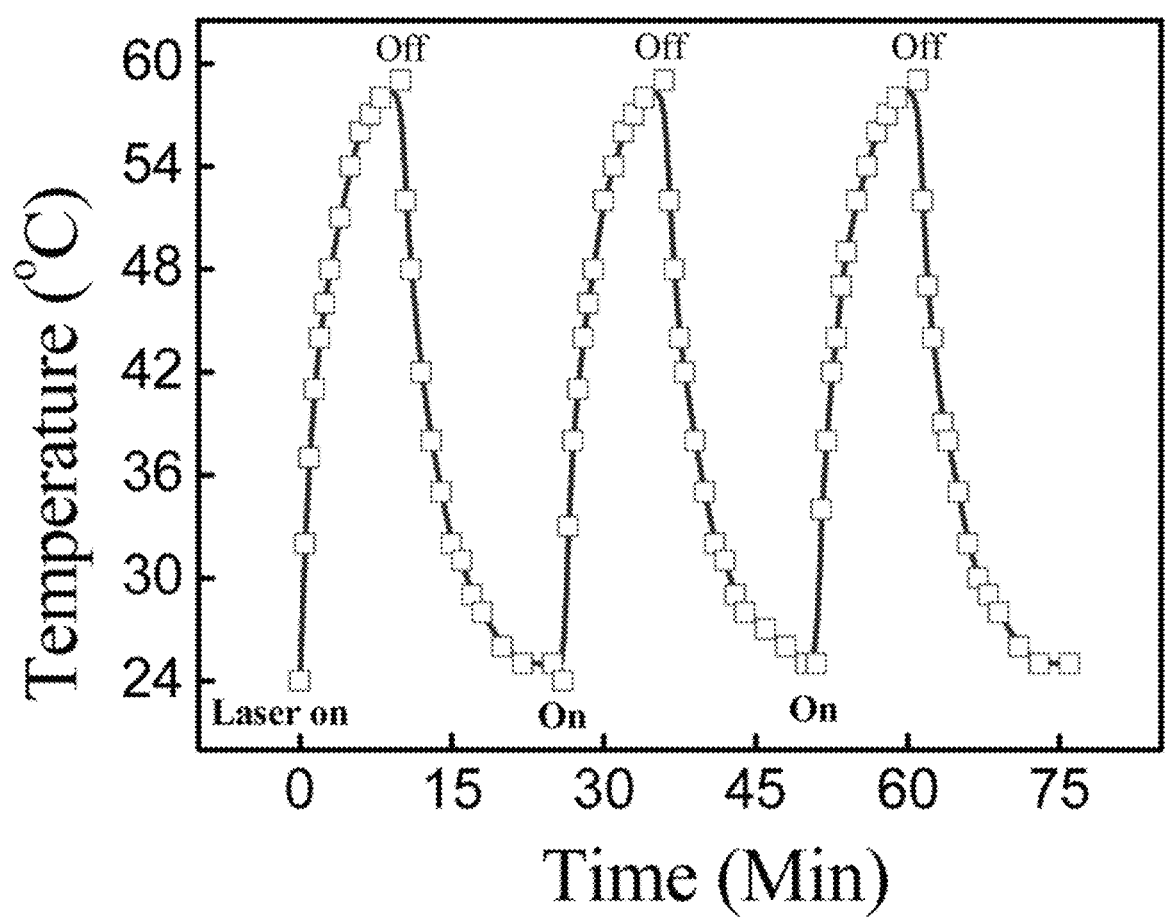
FIG. 5 shows the measured temperature of IONP-Au$_2$S core-satellite nanocomposite in water with repeated laser on and off, indicating that there is no quenching effect, where the diode laser (λ=885 nm) at a fluence rate of 2.5 W/cm$^2$ is used.
Figure 6:
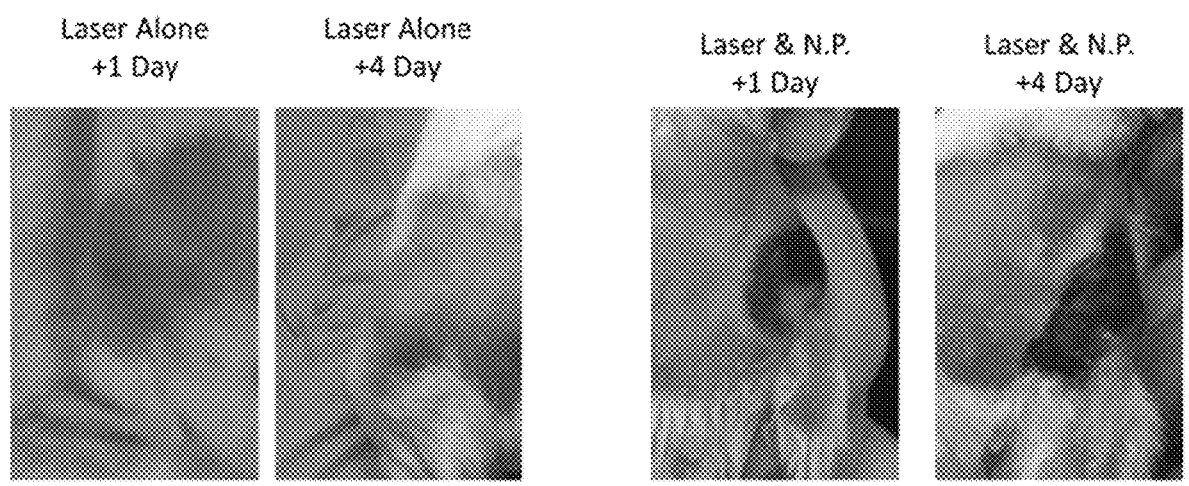
FIG. 6 shows a photograph of a tumor site after laser irradiation, where tumor in the mouse intravenously injected with IONP-Aus core-satellite nanocomposites shows significant damage of blood vessels by laser but not in the control mouse.
Figure 7:
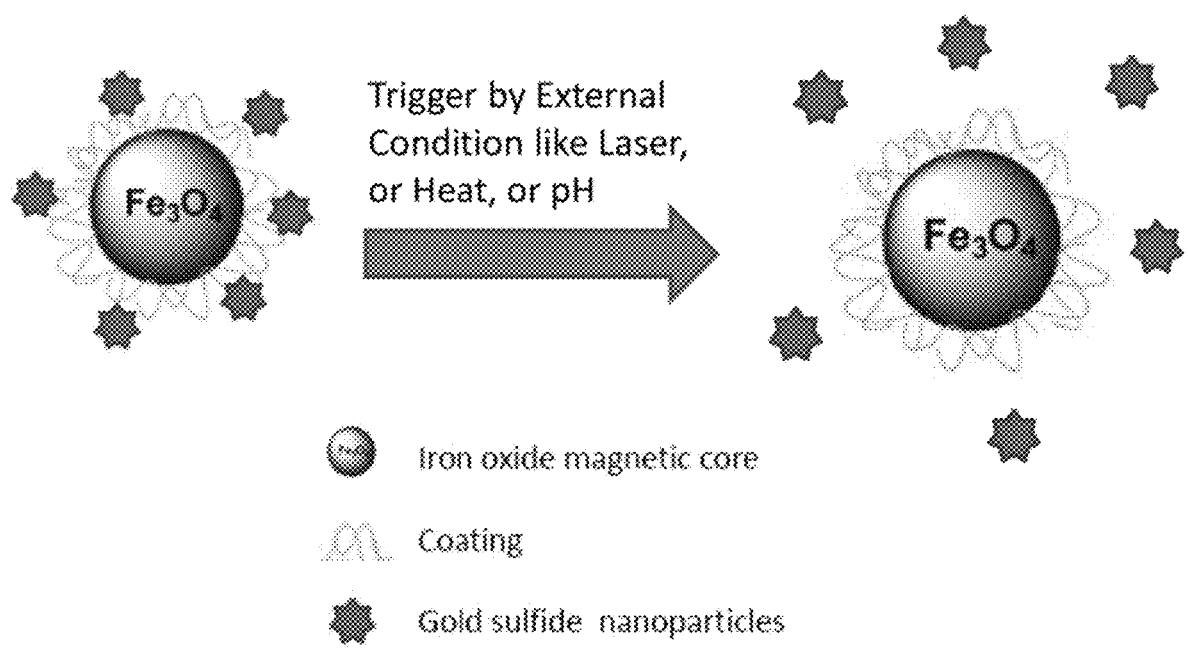
FIG. 7 shows a schematic of releasing satellites triggered by external conditions. These releasable satellite nanomediators have the ability to penetrate deeper into tumor tissue to show better efficacy to kill tumor cells.

The results of the above procedures are shown in the Figures. FIG. 1 shows a TEM image of IONP/$Au_2S$ core-satellite nanocomposite, where the magnetic core is 15 nm in diameter and is further attached with tiny multiple Au2s nanoparticles. FIG. 2 shows an optical spectrum of $Au_2S$ nanoparticles with adjustable peak at near infrared range. $Au_2S$ nanoparticles were produced by mixing $HAuCl_4$ (1.0 mL, 2 mM) and serials of volume of $Na_2S$ (1 mM) in water. In each figure, data were recorded over time until the curve is unchangeable. FIG. 3 shows an absorption spectrum of IONP/$Au_2S$ core-satellite nanocomposite, where the infrared absorption is adjustable by controlling the amount of sodium sulfide. FIG. 4 shows the measured temperature of IONP/$Au_2S$ core-satellite nanocomposite and IONPs only after irradiation with a diode laser ($\lambda$=885 nm) at a fluence rate of 2.5 W/cm$^2$. FIG. 5 shows the measured temperature of IONP/$Au_2S$ core-satellite nanocomposite in water with repeated laser on and off, indicating that there is no quenching effect, where the diode laser ($\lambda$=885 nm) at a fluence rate of 2.5 W/cm$^2$ is used. FIG. 6 shows a photograph of a tumor site after laser irradiation, where tumor in the mouse intravenously injected with IONP/Aus core-satellite nanocomposites shows significant damage of blood vessels by laser but not in the control mouse. FIG. 7 shows a schematic of releasing satellites triggered by external conditions. These releasable satellite nanomediators have the potential to penetrate deeper into tumor tissue to show better efficacy to kill tumor cells.

Figure 14:
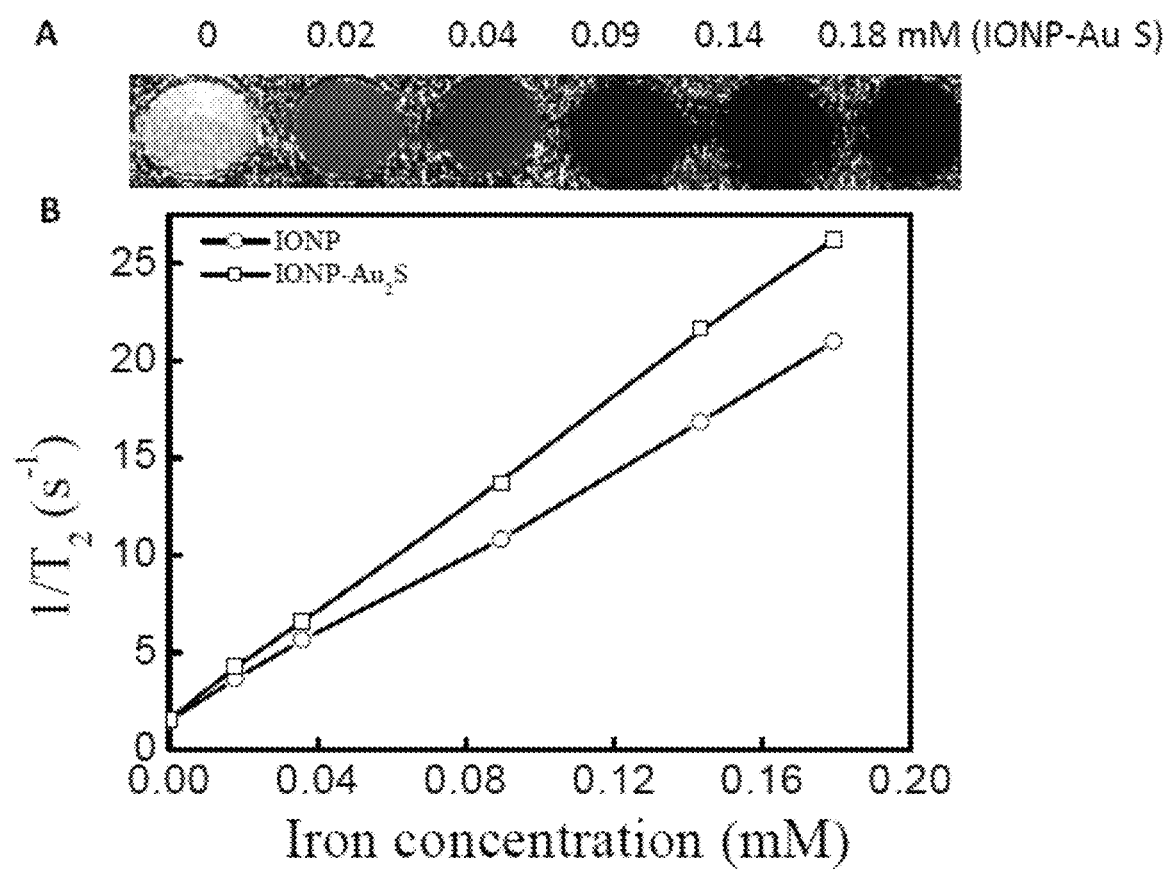
FIG. 14 shows (Panel a) T2-weighted MR images (Panel b) T2 relaxation rates (R2) of IONP/Au2S core/satellites nanocomposite solutions at each iron concentration.
Figure 15:
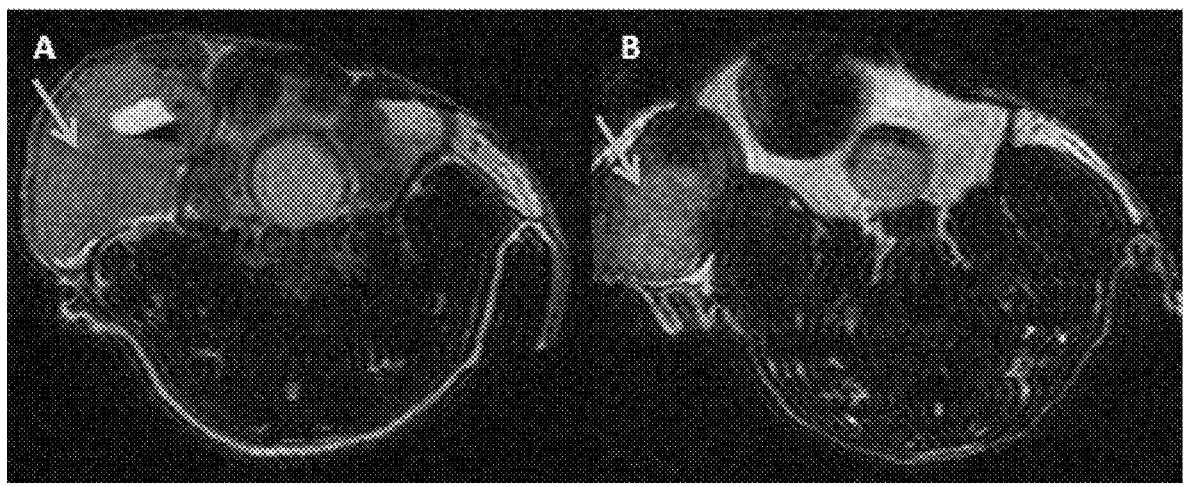
FIG. 15 shows MR images of SUM-159 tumor-bearing mouse intravenously injected with PBS (Panel a) or IONP/Au2S core/satellites nanocomposite (Panel b). Arrows point to tumor sites.
Figure 16:
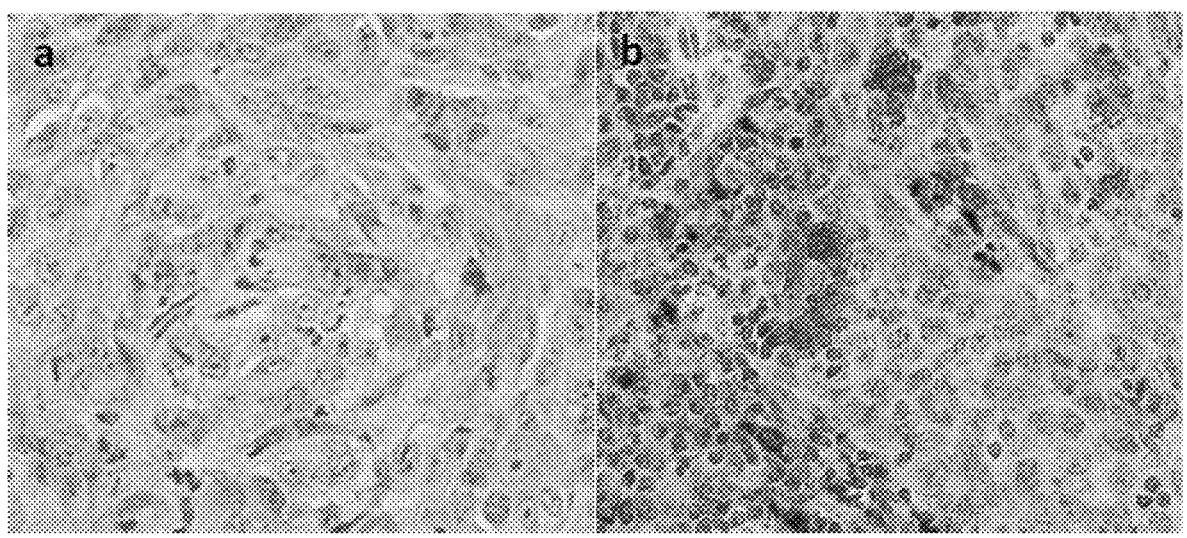
FIG. 16 shows that the presence of IONP/Au2S in tumor was confirmed by Prussian blue staining of histology slides of tumor tissues obtained 24 hours after intravenous injection of PBS (Panel a) and IONP/Au2S nanocomposite (Panel b).
Figure 17:
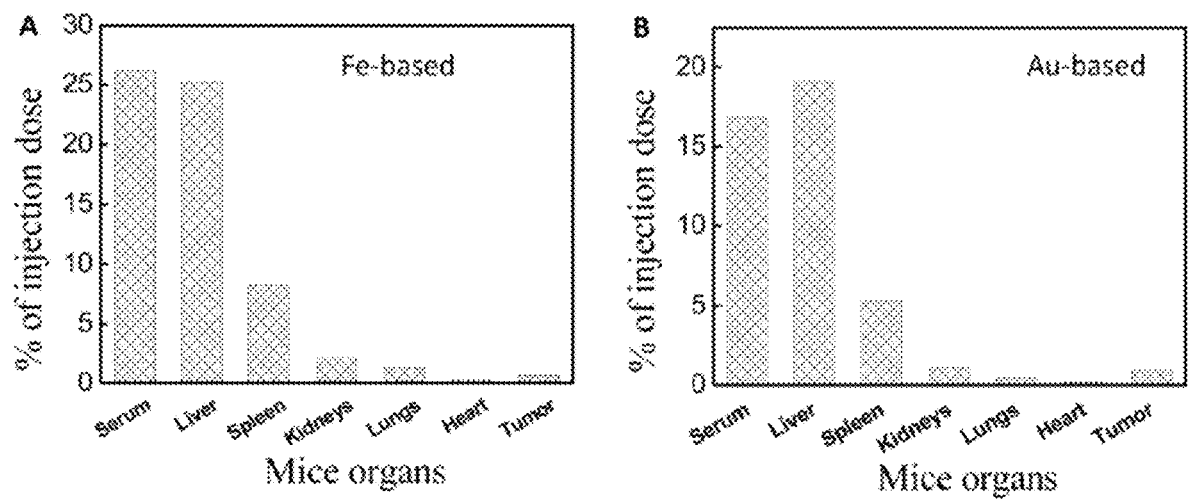
FIG. 17 shows the percentage of injection dose (I.D.) (Panel a, Fe-based analysis and Panel b, Au-based analysis) in tumor-bearing mice main organs at 24 h post intravenous injection of IONP/Au2S nanocomposite. The value shown here has been subtracted with averaged background from control mice. Three mice are in each group.
Figure 18:
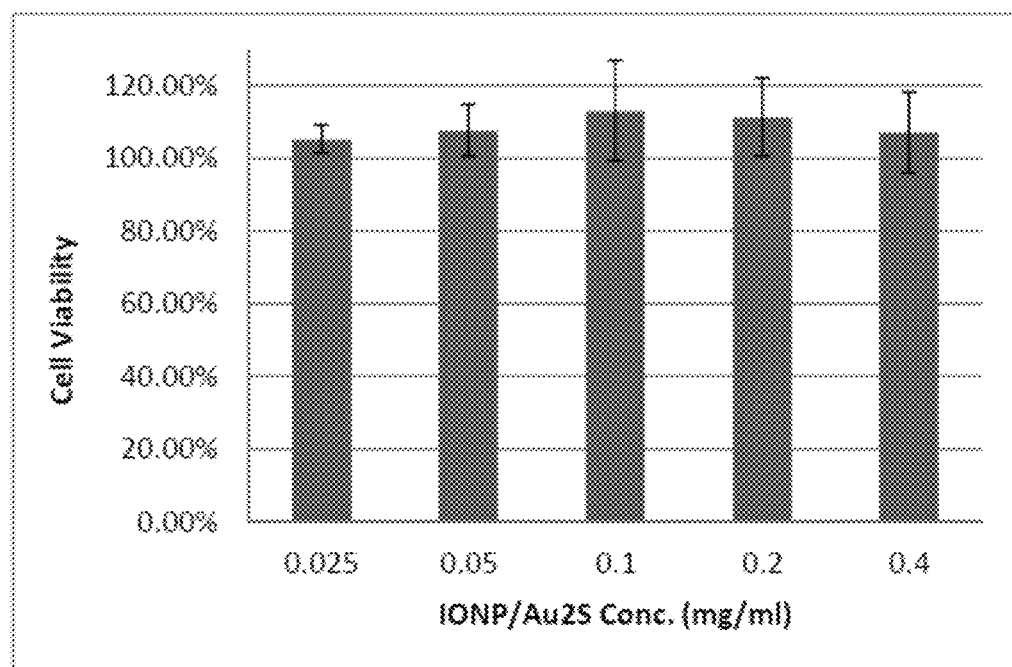
FIG. 18 shows results of a SUM159 cell viability assay. SUM159 cells was not significantly affected by the addition of as prepared IONP/Au2S nanocomposite as all treated group have a viability that is around 100% measured by MTS viability assay after 24 hours of incubation.
Figure 19:
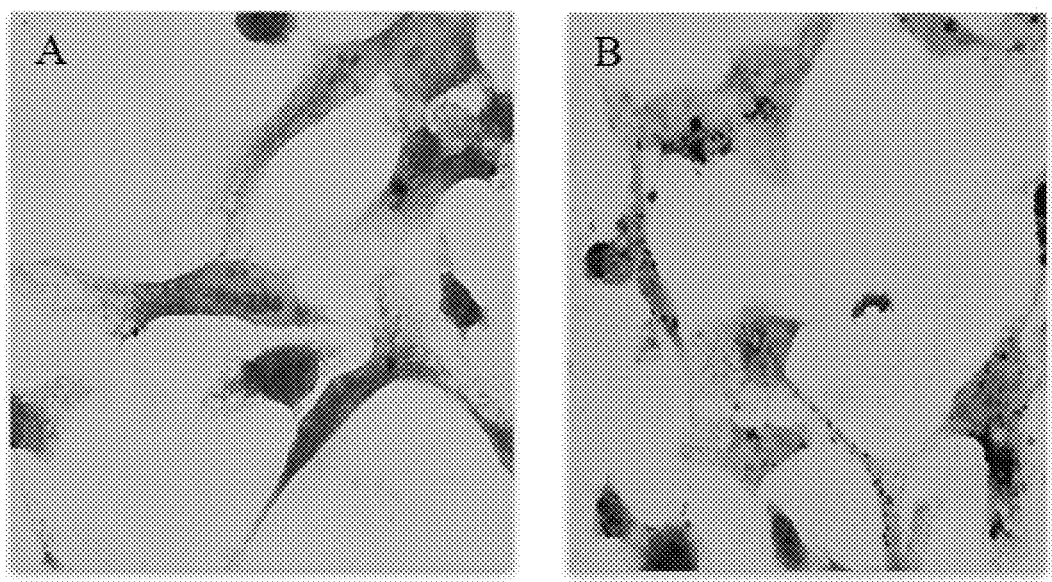
FIG. 19 shows optical microscopy images of SUM159 cell monolayer incubated with the same Fe concentration (0.1 mg/ml) of IONPs (Panel a) and IONP/Au2S core/satellites nanocomposite (Panel b) for 24 h respectively. Fixation was performed by paraformaldehyde and stained with Prissian Blue to visualize iron composition while counter stained with Nuclear Fast Red to show cellular structure. IONPs were stained in blue.
Figure 20:
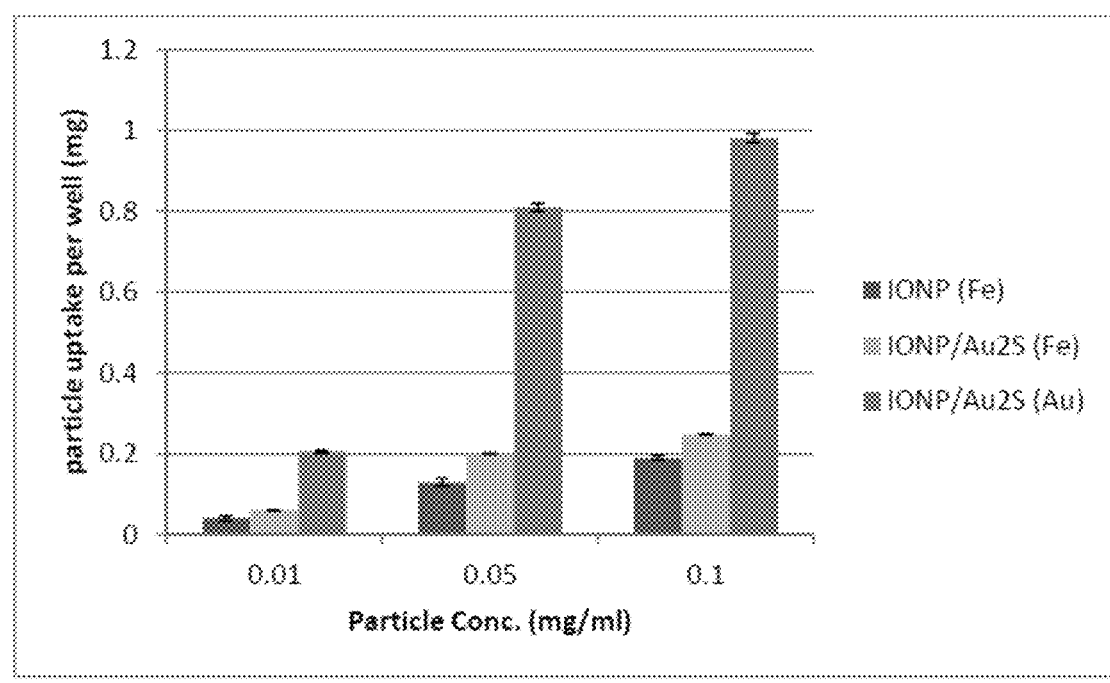
FIG. 20 shows quantitative ICP-OES measurement for IONPs and IONP/Au2S nanocomposite uptake by SUM159 monolayer cells. SUM159 cells uptake more core-satellite structure nanoparticles at relatively higher concentration compared to the even smaller core IONPs.
Figure 21:
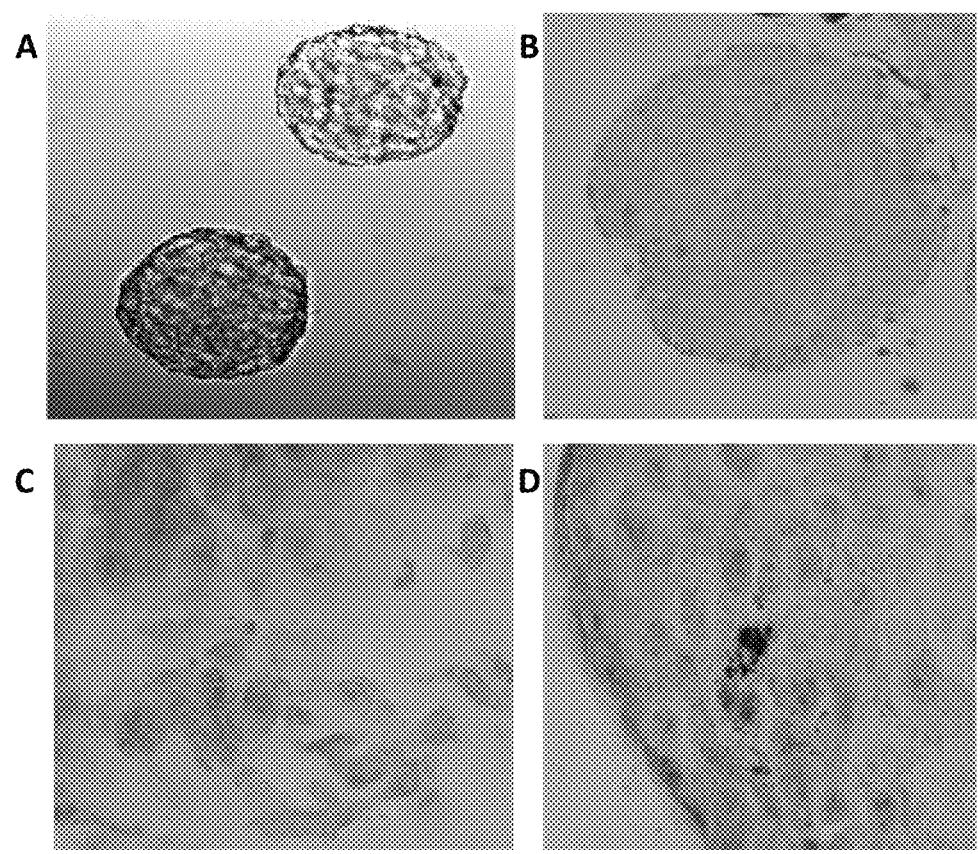
FIG. 21, Panel A shows microscopy image of 7-day-old MCF-7 spheroids seeded at a concentration of 600 cells per well in an ultra-low attachment 96-well plate.
Figure 22:
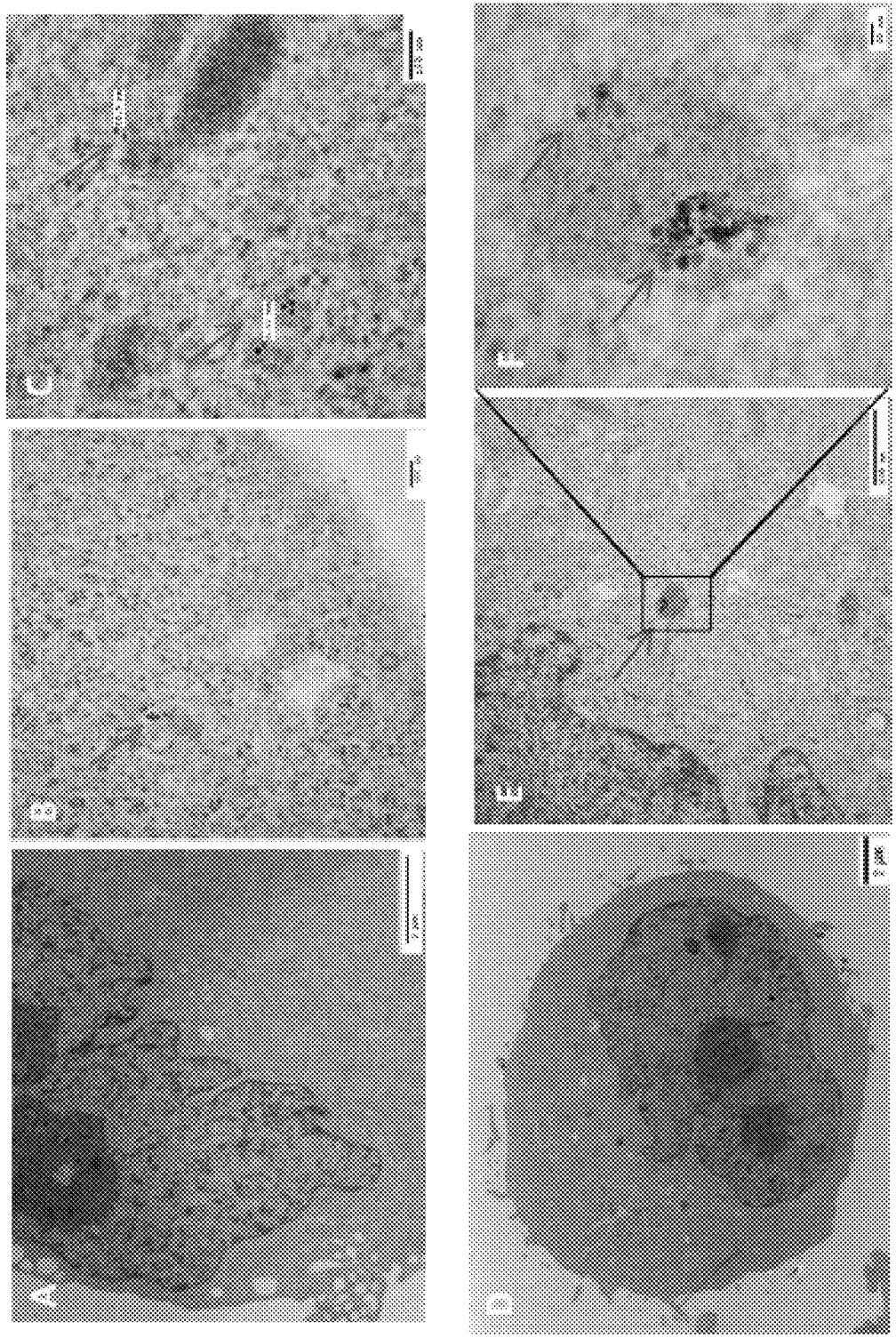
FIG. 22, Panels a-f show TEM images of SUM159 cell monolayer treated with IONPs (upper panels) and IONP/Au2S nanocomposite (lower panels) at the same iron concentration of 0.1 mg/ml for 24 h. Blue arrows point at the IONPs within the cell while the red arrows indicate the IONP/Au2S nanocomposite. Boxed regions are enlarged adjacent panels.

FIG. 14 shows (a) T2-weighted MR images (b) T2 relaxation rates (R2) of IONP/Au2S core/satellites nanocomposite solutions at each iron concentration. FIG. 15 shows MR images of SUM-159 tumor-bearing mouse intravenously injected with PBS (a) or IONP/Au2S core/satellites nanocomposite (b). Arrows point to tumor sites. FIG. 16 shows that the presence of IONP/Au2S in tumor was confirmed by Prussian blue staining of histology slides of tumor tissues obtained 24 hours after intravenous injection of PBS (a) and IONP/Au2S nanocomposite (b). FIG. 17 shows the percentage of injection dose (I.D.) (a, Fe-based analysis and b, Au-based analysis) in tumor-bearing mice main organs at 24 h post intravenous injection of IONP/Au2S nanocomposite. The value shown here has been subtracted with averaged background from control mice. Three mice are in each group. FIG. 18 shows results of a SUM159 cell viability assay. SUM159 cells was not significantly affected by the addition of as prepared IONP/Au2S nanocomposite as all treated group have a viability that is around 100% measured by MTS viability assay after 24 hours of incubation. FIG. 19 shows optical microscopy images of SUM159 cell monolayer incubated with the same Fe concentration (0.1 mg/ml) of IONPs (a) and IONP/Au2S core/satellites nanocomposite (b) for 24 h respectively. Fixation was performed by paraformaldehyde and stained with Prussian Blue to visualize iron composition while counter stained with Nuclear Fast Red to show cellular structure. IONPs were stained in blue. FIG. 20 shows quantitative ICP-OES measurement for IONPs and IONP/Au2S nanocomposite uptake by SUM159 monolayer cells. SUM159 cells uptake more core-satellite structure nanoparticles at relatively higher concentration compared to the even smaller core IONPs. FIG. 21A shows microscopy image of 7-day-old MCF-7 spheroids seeded at a concentration of 600 cells per well in an ultra-low attachment 96-well plate. FIG. 21B shows MCF-7 spheroid incubated in medium after Prussian Blue Staining as a control image. Higher magnification pictures of MCF-7 spheroids treated with IONPs (c) and IONP/Au2S core/satellites nanocomposite (d) after Prussian Blue staining. Iron concentration were kept at 0.1 mg/ml in both groups and iron composition were stained in blue. FIG. 22 shows TEM images of SUM159 cell monolayer treated with IONPs (upper panel) and IONP/Au2S nanocomposite (lower panel) at the same iron concentration of 0.1 mg/ml for 24 h. Blue arrows point at the IONPs within the cell while the red arrows indicate the IONP/Au2S nanocomposite. Boxed regions are enlarged adjacent panels.

Example 2

Nanocarrier Highly Packed with NIR Dyes for Effective Tumor Accumulation and Photothermal Therapy This Examples describes the preparation and characterization of 'stealth' nanocarriers with NIR organic dye for effective tumor accumulation and enhanced PTT.

Experimental Section

Materials

Iron oxide (III) (FeO(OH), hydrated, catalyst grade, 30-50 mesh), oleic acid (technical grade, 90%), 1-octadecene (technical grade, 90%), anhydrous tetrahydrofuran (THF, 99.8%), IR820, (3-mercaptopropyl) trimethoxysilane (MPTS), ammonium iron (II) sulfate hexahydrate (Fe(NH4)2(SO4)2.6H2O, ACS reagent, 99%), o-phenanthroline monohydrate (ACS reagent, 99%), hydroquinone (ACS reagent, 99%), nitric acid (ACS reagent, 70%), and hydrochloric acid (ACS reagent, 37%) were purchased from Sigma-Aldrich and used directly.

Synthesis of IONPs

IONPs (15 nm in diameter) were synthesized in organic solvent by thermal decomposition as reported previously [25]. Briefly, a mixture of 0.890 g FeO(OH), 19.8 g oleic acid and 25.0 g 1-octadecene in a three-neck flask was heated under stirring to 200° C. under N2, 30 minutes late the temperature was set at 220° C. for 1 h, then the temperature was increased gradually to 310° C. (20° C./5 minutes) and kept at this temperature for 1 hour. The solution became black when the temperature was increased to 320° C. and kept at this temperature for 1 h. After the reaction was completed, the reaction mixture was cooled and the nanocrystals were precipitated by adding chloroform and acetone.

Coating of IONPs with Polysiloxane-Containing Diblock Copolymer

Diblock copolymer (PEO-b-PγMPS) was synthesized by the reversible addition of fragmentation chain transfer (RAFT) polymerization as previously reported [26]. The method for coating single core nanocrystals was reported previously [25]. Briefly, the purified nanocrystals (100.0 mg) were dispersed in 10 mL of anhydrous THF and then mixed with the newly synthesized copolymer (1.00 g) in 10 mL of anhydrous THF. After being aged for four days, the mixture was added dropwise into 100 mL of water with gentle magnetic stirring. THF in the solution was removed by dialysis using deionized water. The resultant solution was then purified by using a magnetic separator (Frantz laboratory). This wash-resuspend step was repeated three times. The average hydrodynamic diameter was measured using a dynamic light scattering instrument (Malvern Zeta Sizer Nano S-90). The magnetic nanocrystals were viewed by transmission electron microscopy (TEM) (Philips CM-100 60 kV). UV-vis-NIR spectra were recorded in a BioTek micro-plate reader (Synergy 2) using 200 μL of aqueous solution.

Conjugation of IR820 to Polysiloxane-Containing Polymer Coated IONPs 174.0 mg IR820 was dissolved in 10 mL of anhydrous DMF in a 50 mL flask and the mixture was purged with N2 for 1 h. Then 120 ul of MPTS was added and the reaction was carried out at room temperature overnight in the dark. The resultant mixture was then added into the mixture of diethyl ether/ethanol (v/v: 10/1). The precipitants were washed with ether and then 2.5 ml of DMSO was added to dissolve the pellet. The residue of ether was removed by evaporator under reduced pressure at room temperature. The freshly made MPTMS modified IR820 (1.3 mL) was mixed with 5 mL of polymer-coated IONPs in borate buffer (50 mM, pH 8.0) overnight in the dark at room temperature. The resultant system was applied to successive centrifugation at 22,000 rpm for 1 h (Allegra™ 64R Centrifuge). The supernatant was collected for measuring the unbound IR820 concentration and the pellet was suspended in borate buffer.

Determination of Iron Concentration Using Spectrophotometry

10 μL of concentrated IONP or IONP-IR820 solutions was diluted with 2 mL of Milli-Q water, followed by adding 200 μL of concentrated HCl solution. After two days, sodium citrate was added to adjust the solution pH to 3.5. Then 2 mL of hydroquinone (10 g/L) and 3 mL of ophenanthroline (2.5 g in 100 mL of ethanol and 900 mL of water) were added to the solution followed by adjusting to a specific volume using Milli-Q water. Five standard Fe solutions using Fe(NH4)2(SO4)2.6H2O were also made. To determine the solution concentration of iron, calibration curves were generated by measuring optical absorbance of solutions at 508 nm.

Photothermal Effect of IONP-IR820 in Aqueous Solutions

To study the photothermal effect of IONP-IR820 induced by NIR light, the aqueous solutions (1.0 mL) of the nanocomposite with Fe concentration at 0.2 mg/mL in a cuvette were irradiated using an NIR laser (885 nm, spot size, 5×8 mm2, MDL-III-885, OPTO Engine LLC, Midvale, Utah) for 10 minutes with four different laser power settings (1.0, 0.5, 0.2, and 0.1 W). The laser power at 0.5 W was set for the rest of the experiments including in vivo studies. The temperature of the solutions was measured by a digital thermometer.

Cell Culture

SUM-159 cells were cultured under a 5% CO2 environment in F12 media (Invitrogen, Carlsbad, Calif.) supplemented with 5% fetal bovine serum (Fisher Scientific, Pittsburgh, Pa.), 1% antibioticantimycotic (Invitrogen, Carlsbad, Calif.), 5 μg/mL insulin (Sigma-Aldrich, St Louis, Mo.), 1 μg/mL hydrocortisone (Sigma-Aldrich, St Louis, Mo.), and 4 μg/mL gentamicin (Invitrogen, Carlsbad, Calif.).

Xenograft Mouse Model

All studies involving mice were conducted in accordance with a standard animal protocol approved by the University Committee on the Use and Care of Animals at the University of Michigan. Five week old nude mice were obtained from Charles River Breeding Laboratories. Xenograft formation was generated by direct injection of 5×10$^5$ SUM-159 cells, suspended in matrigel, into the exposed no. 4 inguinal mammary pad. Tumor detection was assessed by palpation and once identified measurement of tumor volume was carried out using digital calipers and calculated by volume= (width)2×length/2.

Biodistribution

SUM-159 tumor-bearing nude mice were used for this study. Mice in one group (three mice in each group) were intravenously injected with IONP-IR820 at dose of 20 mg Fe/Kg mouse body weight. Mice in another group were used as a control without any injection. After 24 hours, animals were sacrificed. Blood samples were collected by terminal heart puncture and centrifuged for 10 minutes at 5,000 rpm to separate the serum. The tissue samples of tumor, liver, spleen, lungs, kidney, heart, brain, stomach, and muscle were collected and weighed. To determine the iron concentrations in the serum or major organs, 200 μL of serum or whole organ tissue samples were digested in 1 mL of nitric acid (2 mL for liver). After filtration (acrodisc syringe filters, PTFE membrane, diameter 13 mm, pore size 0.45 μm), the volumes of solutions were adjusted to 10.0 mL and the iron concentration was analyzed using inductively coupled plasma optical emission spectrometry (ICP-OES) with Yttrium as the internal standard.

In Vitro MRI and T2 Relaxivity Measurement

Magnetic resonance imaging (MRI) studies were carried out by using a MRI scanner at 7.4-T field strength. For T2 measurements, a multiecho fast spin-echo sequence was used to simultaneously collect a series of data points at different echo times (TE=15-90 ms with an increment of 15 ms). The T2 relaxation time of each nanoparticle sample was calculated by fitting the decay curve on a pixel-by-pixel basis by using a nonlinear monoexponential algorithm M(TE)=M0 exp(-TEi/T2), where TE is the echo time, M(TE) is the MRI signal intensity at which TE is used.

MRI of Tumor-Bearing Mice

Tumor-bearing nude mice 24 hours post intravenous injection (IONP-IR820, IR820, IONP, and PBS) were scanned with a wrist coil to collect contrast enhanced MRI data. T2 weighted fast spin echo sequence was used to obtain T2 relaxometry of the tumor tissue. The averaged signal intensity of whole tumors was calculated manually using ImageJ (U.S. National Institutes of Health, Bethesda, Md., USA) for comparing the signal intensity before and after injection of magnetic nanoparticles.

In Vivo PTT

Tumor-bearing nude mice were randomly allocated into three groups (five mice in each group) when the solid SUM-159 tumors had grown to ~80 mm3. Mice in each group were intravenously injected with IONP-IR820 (20 mg Fe/Kg mouse body weight), the same amount of IR820, the same amount of IONPs. 24 h post injection, tumors were irradiated with a diode laser (λ=885 nm) at a laser power of 0.5 W for 10 minutes. The highest tumor surface temperature was recorded by an infrared camera (FLIR Systems, i7, Boston, Mass.) before and after application of the laser.

Histology

Mice were humanely euthanized by CO2 inhalation 24 h following a single I.V. bolus dose of nanoparticles. The harvested tissue was formalin-fixed, embedded in paraffin and sectioned. Unstained slides were dewaxed using xylene and rehydrated using graded alcohol. Rehydrated slides were stained with Hematoxylin and eosin (H&E staining) for visualization of nucleic acids and cytoplasm.

Statistical Analysis

Differences in biodistribution data were analyzed using a two-tailed unpaired Student's t-test, with p<0.05 considered statistically significant.

Results and Discussion

Preparation of IONPs Densely Packed with IR820

Figure 8:
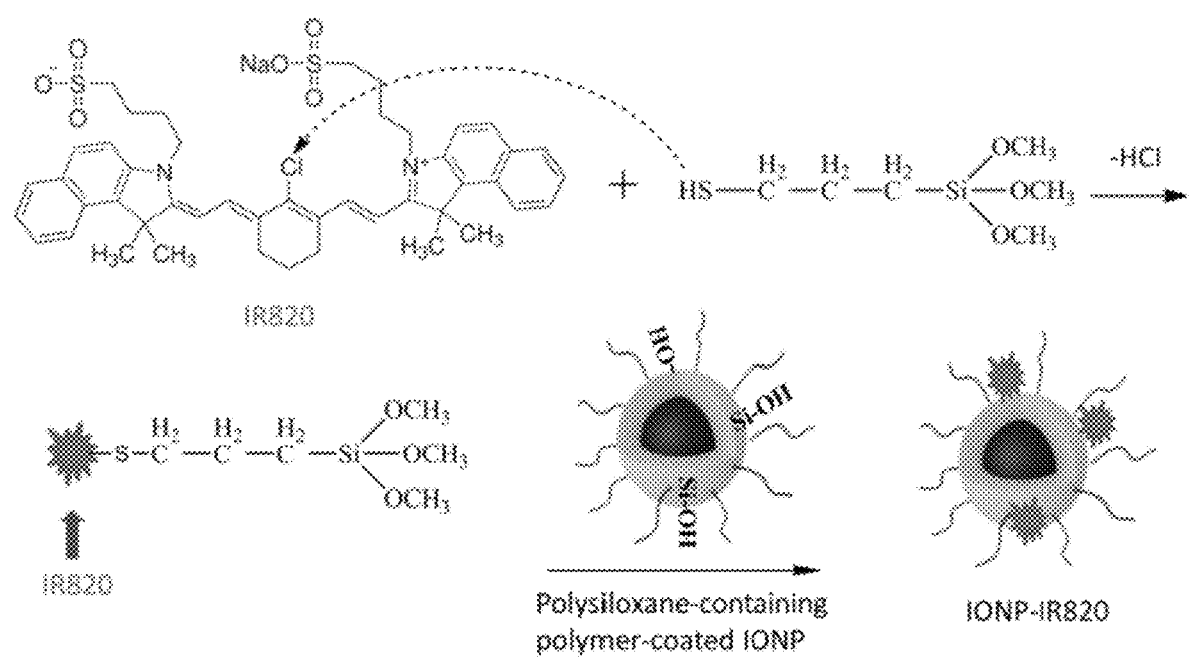
FIG. 8 shows a schematic of magnetic nanoparticles conjugated with near infrared dye (such as IR820) for dual imaging (MRI and optical) and dual photothermal effect capabilities (from IONP core and NIR dye).

Magnetic IONPs further coated with polysiloxane-containing block copolymer have been proved as PTT mediators. The high crystallinity of IONPs and antifouling polymer coating as well as small overall size enabled efficient photothermal cancer therapy using IONPs in mouse tumor models. In this Example, such a "stealth" nanocarrier was modified with NIR organic dye for effective tumor accumulation and enhanced PTT. IR820, as an analogue to indocyanine green (ICG), has strong absorption around 800 nm and have been widely used as imaging probes and PTT mediators [22, 27]. Different from ICG, IR820 has a reactive chlorine group for further modification [28, 29]. In this example, IR820 was modified with (3-mercaptopropyl) trimethoxysilane (MPTS) to further conjugate to polysiloxane-containing polymer coated IONPs through siloxane crosslink as shown in FIG. 8. The resultant IONPIR820 nanocomposite was purified through successive centrifuge to get rid of unbound IR820.

Figure 9:
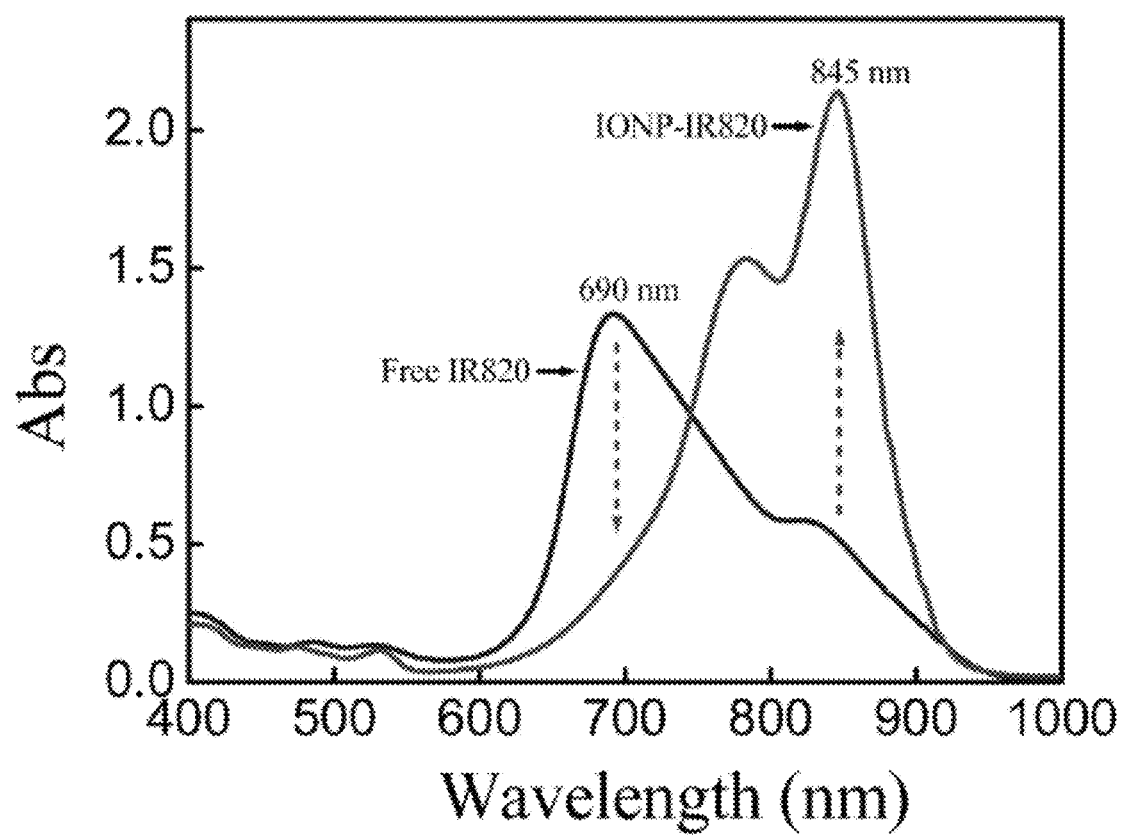
FIG. 9 shows absorption spectrum of IR820 only and IONP-IR820 conjugate. By measuring the free IR820 concentration in the supernatant, it was estimated that the IR820 density on each IONP is 2×104 IR820 on average. In IONP-IR820 sample, the IR820 concentration: 32.6 uM.

The successful conjugation of IR820 onto polysiloxane-containing polymer coated-IONPs was confirmed by the absorption spectrum (FIG. 9). It shows that the purified nanocomposite has strong absorption over 700-900 nm, which is absent from unmodified IONPs [25]. Compared to free IR820, which has a strongest absorption peak at 690 nm, the highest peak from conjugated IR820 is located at 840 nm. This is not a Stoke's peak shift but rather a suppression of absorption over 690 nm and a boost of absorption over 840 nm from IR820 after conjugation. This phenomenon is similar to previous findings and is believed to be caused by the chemical environment around the dye.

The density of IR820 on each IONP is quantified by measuring the concentration of the free dye leftover in the supernatant after centrifugation through a calibration curve. It is estimated that around $2 \times 10^4$ IR820 per IONP. It is believed that the dye density on nanoparticle can be simply adjusted through controlling the feeding ratio of IR820/IONP. While the present invention is not limited to any particular mechanism, it is believe that the high pack density is probably attributed to the large amount of —SiOH groups from the original polymer coating and also from newly conjugated siloxane modified IR820. Although it is densely loaded with IR820 molecules, the resultant nanocomposite's hydrodynamic size as measured by DLS shows little change compared to unmodified IONPs as summarized in Table 1.

TABLE 1

Comparison of physical characterization of IONP and IONP-IR820.

| Samples | Number weighted Hydrodynamic size (nm) | Zeta potential (mV) | Molar ratio of IR820/IONP |
|---|---|---|---|
| IONP | 24.4 ± 0.2 | −14.0 ± 0.3 | N/A |
| IONP-IR820 | 28.2 ± 0.5 | −57.4 ± 1.2 | $2 \times 10^4$ |

Figure 23:
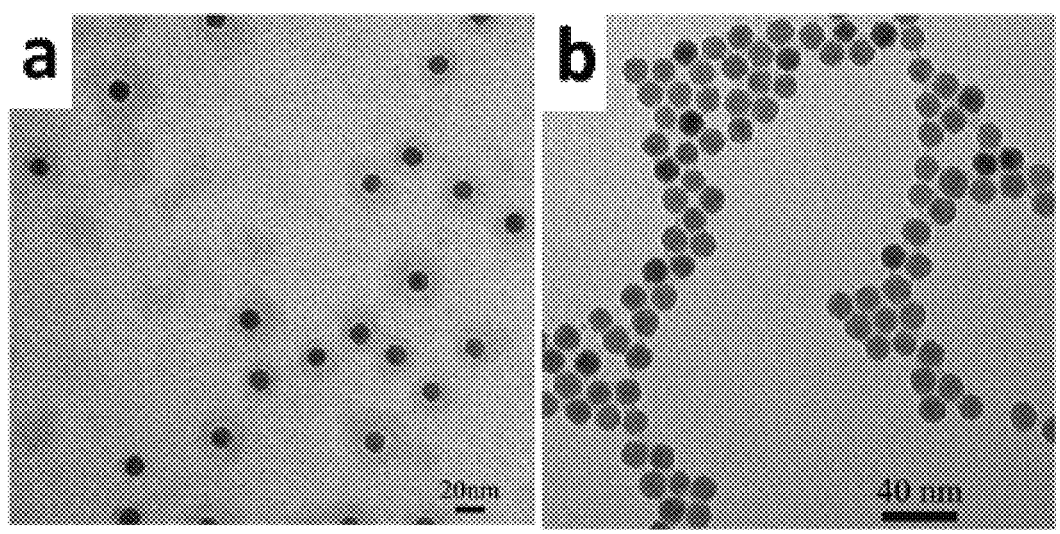
FIG. 23, Panels a-b show TEM images of IONP and IONP-IR820 conjugate.

Interestingly, the zeta potential shows highly negative surface charge (−57.4±1.2 mV) compared to IONPs only (−14.0±0.3 mV) at pH 8.0 (borate buffer, 50 mM), revealing the existence of negative charged IR820 on the surface. TEM image of IONP-IR820 nanocomposite shows that they are individually dispersed (FIG. 23). Different from unmodified IONPs, which connect each other when they dry out on TEM grid (10), they separate from each other, which is probably attributed to the highly charged surface and so the strong repulsion between nanoparticles.

Photothermal Effect of IONP-IR820 in Solutions

Figure 10:
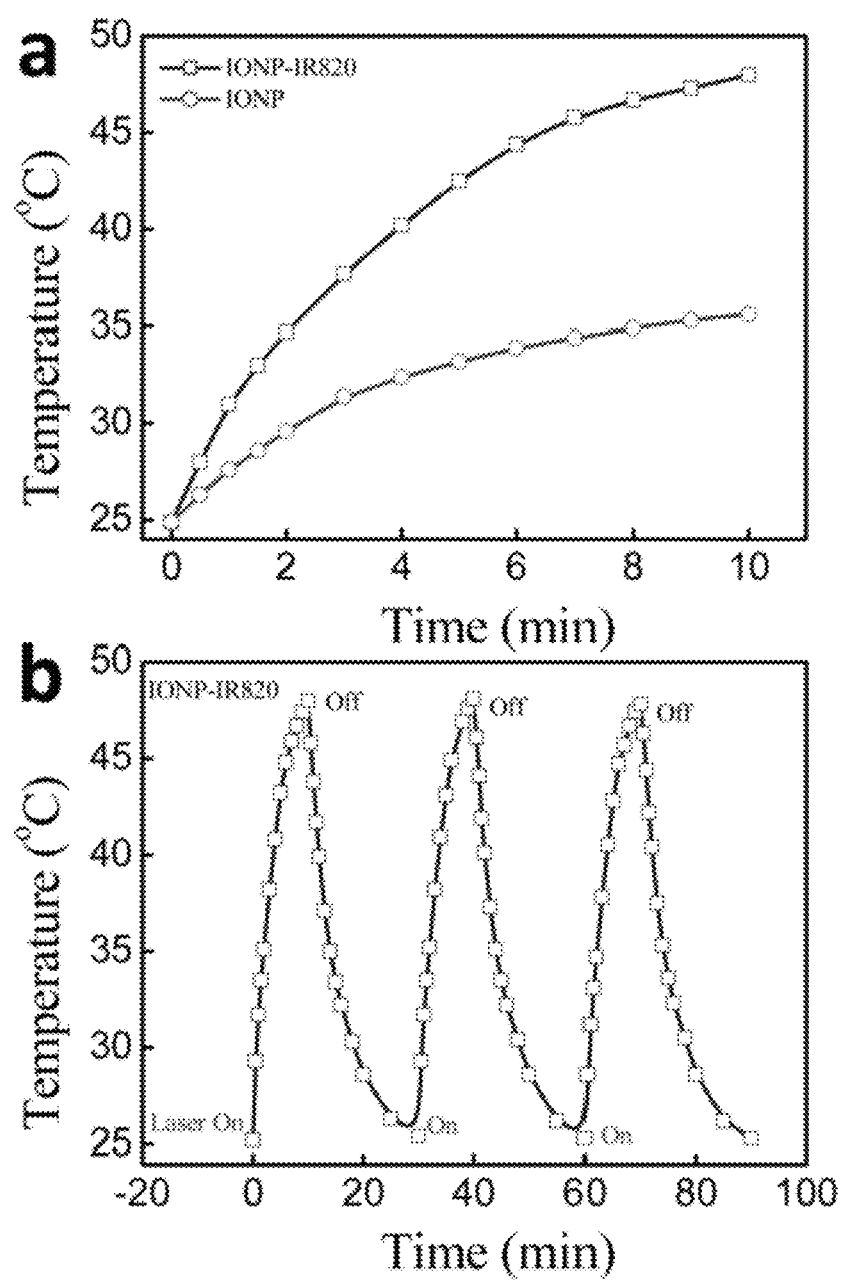
FIG. 10 shows: (Panel a) a comparison of photothermal effect of IONP-IR820 conjugate and IONP only in solutions, where the laser power is 0.5 W; and (Panel b) temperature change of IONP-IR820 over three on/off cycles of NIR laser irradiation.
Figure 11:
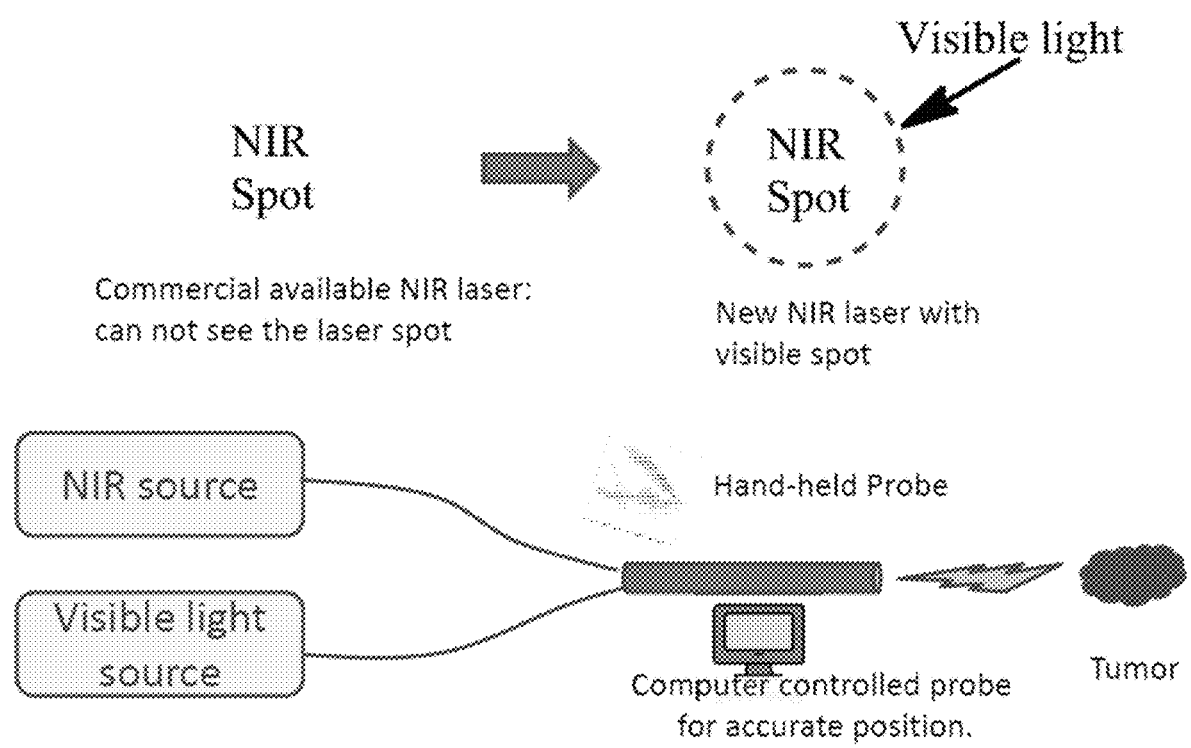
FIG. 11 shows one exemplary design of a NIR laser with visible light component to generate a visible spot where the NIR laser is shining on a subject.
Figure 12:
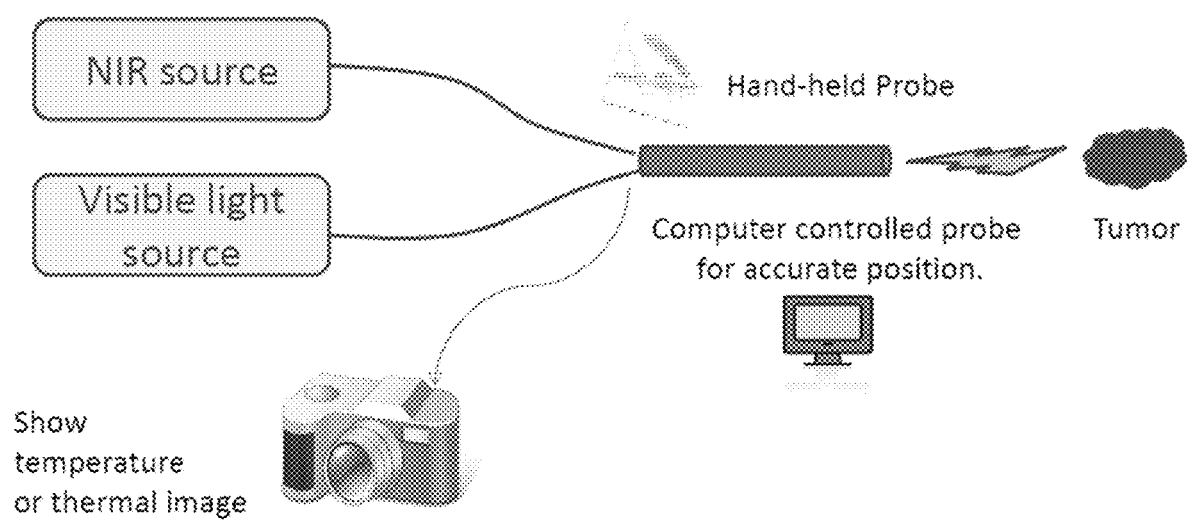
FIG. 12 shows one exemplary design of a NIR laser with the ability to show the real-time temperature profile, combined with an infrared camera.

After modification with IR820, IONPs show enhanced photothermal effect dramatically. Using the same laser and power, it is proven that the IONP-IR820 can cause the solution (1.0 mL in a cuvette) temperature increase from 25.2° C. to 69.0° C. after 10 minutes of laser irradiation at a nanoparticle concentration of 0.2 mg Fe/mL, while for IONP solution, the temperature could only be increased to 45.6° C. [25]. By using IONPs highly packed with IR820, one is now able to reduce laser power but still gain significant temperature increase. Laser power was reduced to 0.5 W to shine the same solution, and the data shows that the temperature still could reach 48.0° C., while for IONPs only, the temperature was increased to 35.6° C. as shown in FIG. 10, Panel a. By comparing the photothermal effect from the other lower laser power (0.2 and 0.1 W), the laser power was chosen at 0.5 W for the following experiments including in vivo studies. This data also confirmed that IONP-IR820 nanocomposite shows good photostability against at least three-repeated cycles of laser irradiation (FIG. 10, Panel b). This is consistent with previous work which showed that photostability of organic NIR dyes could be improved if they are encapsulated into micelles [21, 23].

Biodistribution of IONP-IR820 in Tumor-Bearing Mice

Successful PTT in vivo generally requires effective accumulation of nanomediators to tumor sites after intravenous injection. Very often, these nanomediators were injected directly into tumor tissue to achieve high concentration locally [8, 16, 21, 23, 30-32]. So it is still a challenge in nanomedicine to selective deliver nanoparticles to tumor tissue after IV administration. It is generally believed that nanoparticles with the small overall size and the antibiofouling polymer coating are particularly well suited for effective tumor accumulation via the EPR effect [33, 34]. So these small, photo-stable IONP-IR820 nanocomposite are well suited for in vivo PTT.

Figure 24:
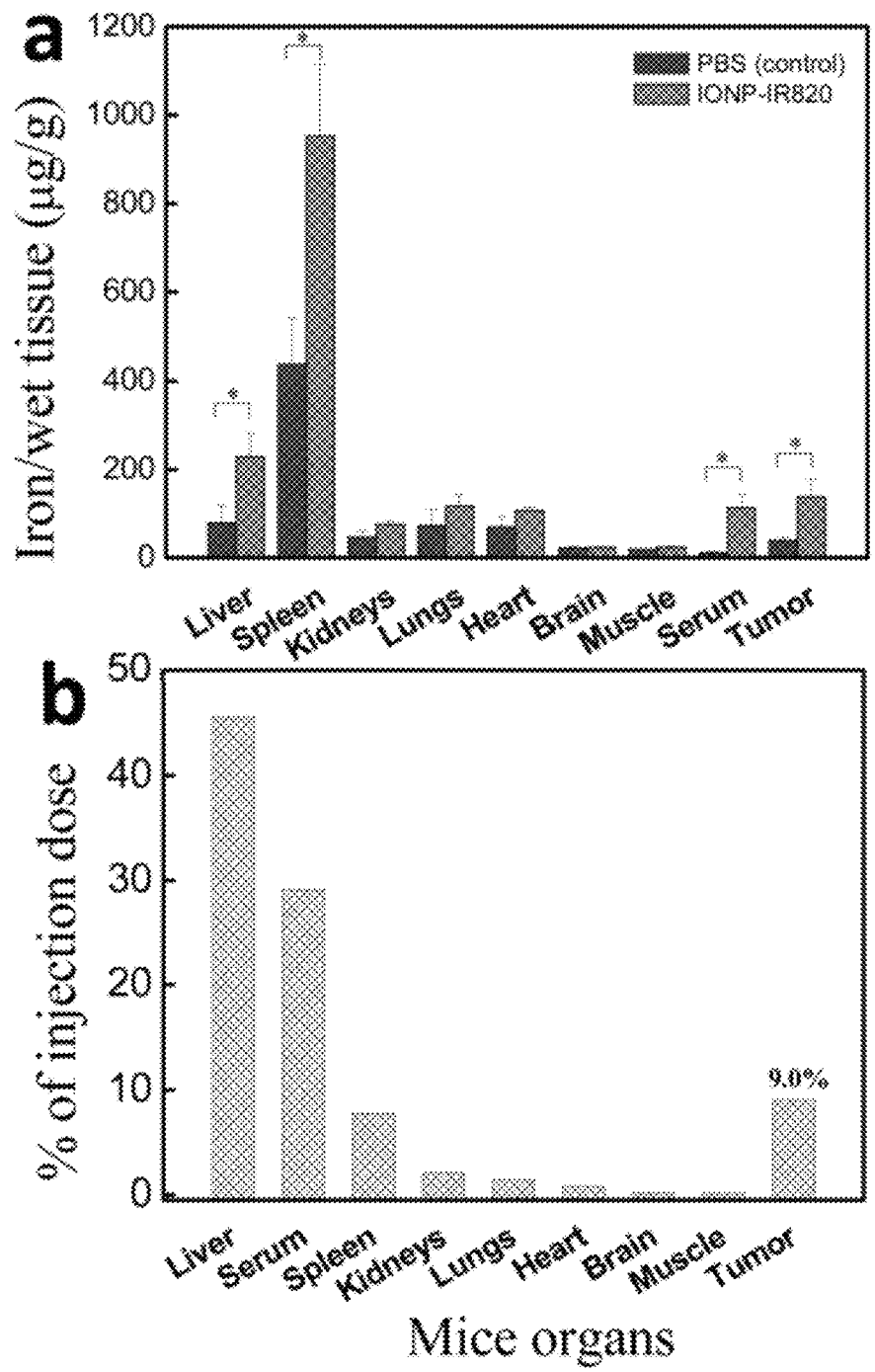
FIG. 24 shows: (Panel a) Biodistribution of IONP-IR820 in main organs 24 h post intravenous administration. Three mice are in each group. Star indicates that the p-value between the two set of data is smaller than 0.05. (Panel b) Percentage of injection dose (ID) in main organs at 24 h post intravenous injection of IONP-IR820. The data showed here is already subtracted from the base line of each organ from PBS control mice.

The biodistribution of IONP-IR820 nanocomposite was evaluated in tumor bearing mice. 24 h post injection, major organs and serum were collected, weighed, and digested with nitric acid and then analyzed by inductively coupled plasma optical emission spectrometry (ICP-OES). Both iron concentration in wet tissues and percentile of injection dosage (% ID) after subtraction of background from non-injected control mice are presented in FIGS. 24a and 24b, respectively. After 24 h circulation post intravenous injection of IONP-IR820, iron concentrations in Serum is 8.3 times higher than control and 30% ID are still circulating in bloodstream, indicating that the administered IONP-IR820 nanoparticles are not cleared out of bloodstream quickly due to the antifouling property of IONPs. The data also shows that the tumor tissue from the same group of mice is 2.5 times higher than the control mice and 9% ID are accumulated in tumor tissue, indicating that IV injected nanomediators can effectively accumulate at tumor tissue by taking advantage of EPR effect. Interestingly, such a tumor accumulation is even much higher than unmodified IONPs, which is only 5.3% ID shown in a previous report. As generally expected, iron concentration in liver is 1.9 times and spleen is 1.2 times higher than their control mice. After 24 h circulation, liver as the biggest organ has 45% ID and spleen has 7.8% ID. Nanoparticles trap in these two organs are higher than the administration of unmodified IONPs (22% in liver and 4.3% in spleen) [25], indicating that highly charged surfaces promote the recognition by immune cells.

MRI Imaging of Tumors

Figure 25:
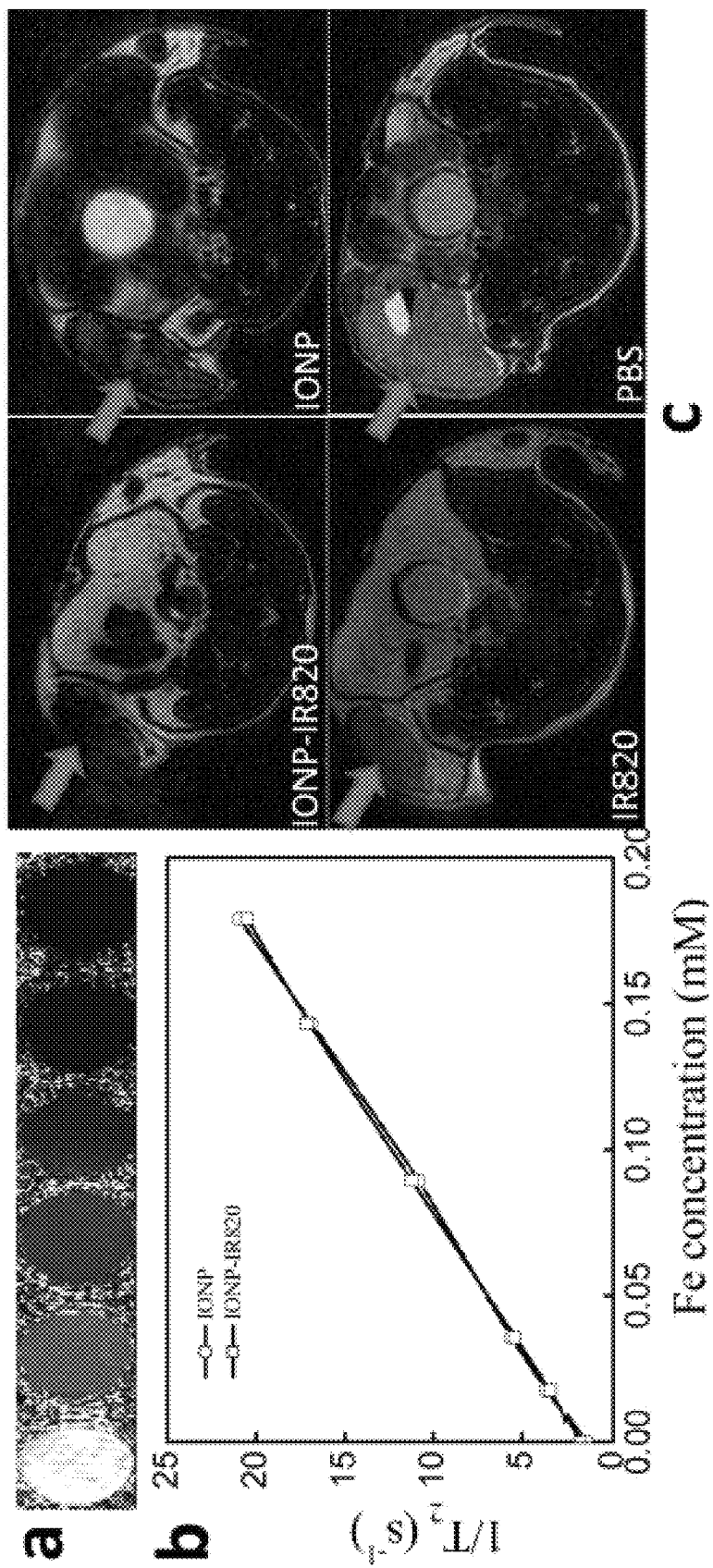
FIG. 25 shows: (Panel a) T2-weighted MR images of IONP-IR820. (Panel b) T2 relaxation rates (R2) of IONP and IONP-IR820 solutions. (Panel c) MR images of SUM-159 tumor bearing mice 24 h after tail-vein injection of IONP-IR820 and three controls.

Developing effective photothermal mediators with MRI imaging capability is highly desired because one can locate tumor and monitor therapeutic effect non-invasively [16-18, 35, 36]. To assess the multimodality properties of as-prepared IONP-IR820, their functionality was tested as MRI imaging contrast agents. T2-weighted MR images of nanocomposite at increasing concentrations from zero to 0.18 mM reveal the concentration-dependent darkening effect (FIG. 25a). FIG. 25b shows that there is little change in the measured transverse relaxivity (r2 at 87.4 mM-1S-1) from IONP core after densely packed IR820 compared to IONP only, consistent with the previous reports [35]. This was then followed by in vivo evaluation of the T2 weighted MR imaging capability. MR imaging of SUM-159 tumor-bearing mice was conducted after intravenous injection of IONP-IR820, unmodified IONP, free IR820, and PBS, respectively as shown in FIG. 25c. Clearly the tumor tissues from mice administered with both IONP-IR820 and unmodified IONPs show an obvious darkening effect compared to the other two control tumor tissues. This suggests that IONPs densely packed with IR820 could be used, in some embodiments, to both induce and monitor the photothermal therapeutic effect.

In Vivo PTT Using IONP-IR820

Figure 26:
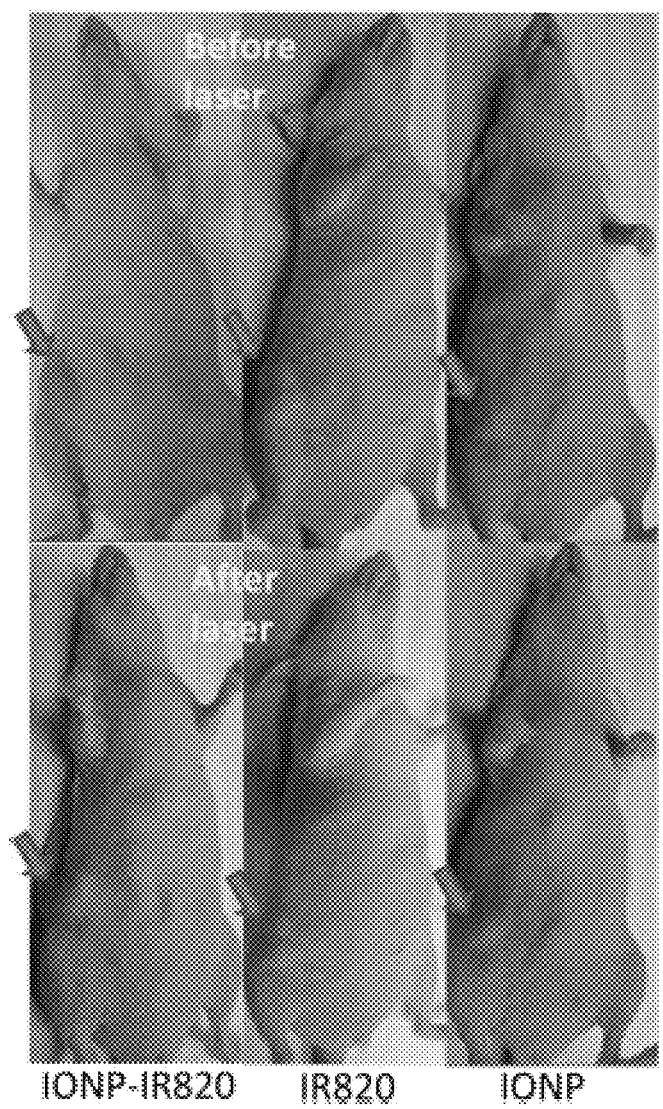
FIG. 26 shows representative photos of SUM-159 tumor-bearing mice of before and right after laser treatment 24 h post intravenous injection of IONP-IR820 and two other controls. Arrow points the tumor site. Laser power: 0.5 W; laser treat: 10 min.
Figure 27:
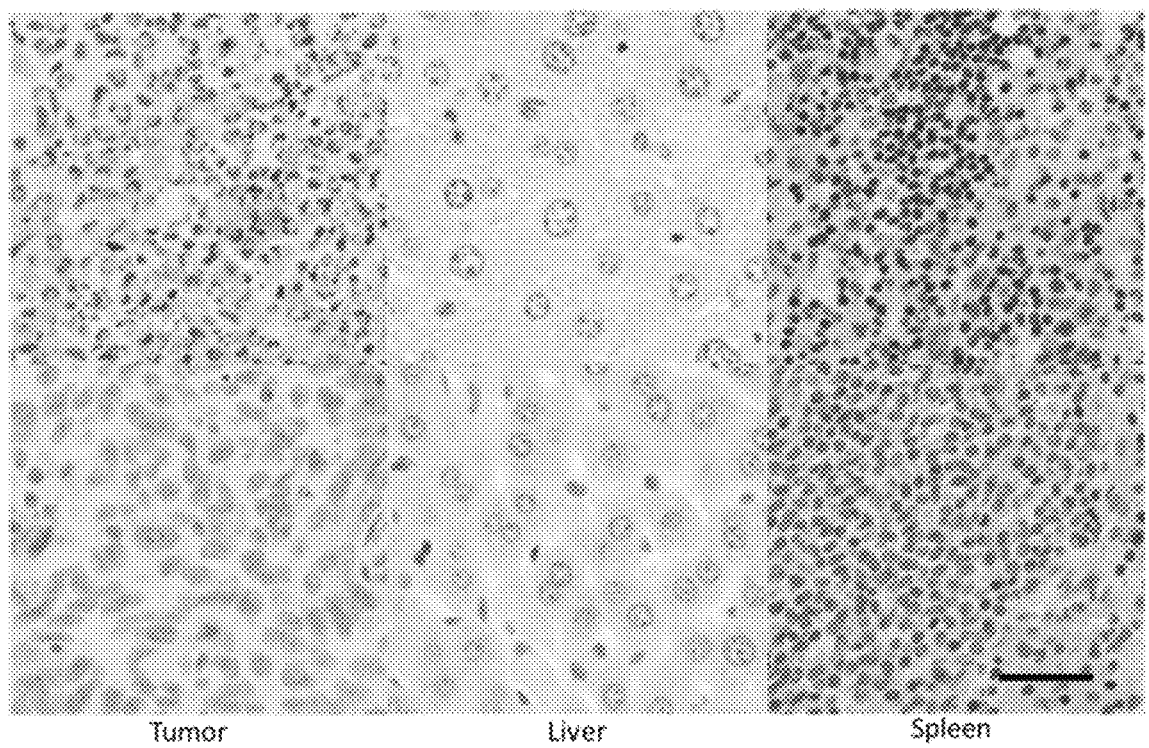
FIG. 27 shows H&E staining of tumor tissues, liver, and spleen from mice treated with IONP-IR820 plus laser irradiation (top panel) and control group treated with laser only (bottom panel). Scale bar: 50 μm.

In vivo PTT was studied using as-prepared IONP-IR820 administered to human xenograft bearing immunocompromised mice. Nude mice bearing SUM-159 tumors were intravenously injected with IONP-IR820 (a dose of 20 mg Fe/Kg mouse body weight) or identical amount of free IR820 or the same amount of IONPs as control. FIG. 26 shows representative photos of tumor-bearing mice before after laser treatment. For the mice administered with IONP-IR820, it is visible by the naked eye that the tumor tissues clearly become blackish 24 h post tail vein injection before laser treatment, indicating that significant amount of IONP-IR820 were accumulated in tumor tissue. In contrast, there is no obvious change at tumor tissues from control mice as shown in top panel of FIG. 26. Tumors were then irradiated with the same laser conditions as in the above in vitro solution study. For the mice intravenously injected with IONP-IR820 tissue hemorrhaging was observed right after laser irradiation for 10 minutes, revealing the damage of tumor blood vessels by the heated nanoparticles around them. In marked contrast, for the control mice exposed to the laser but only injected with IR820 or IONPs, the tumor tissue does not have any obvious hemorrhaging after laser treatment. Haematoxylin and eosin (H&E) stained tumor slices further reveal obvious necrosis of tumor tissue immediately following photothermal treatment for the mice injected with IONP-IR820 relative to control normal tumor tissue as shown in FIG. 27. The data also suggest that the liver and spleen tissues from the mice injected with IONP-IR820 show little change compared to the control mice based on the H&E staining. These data clearly demonstrate that IONP-IR820 nanocomposites function as effective PTT agents.

Figure 28:
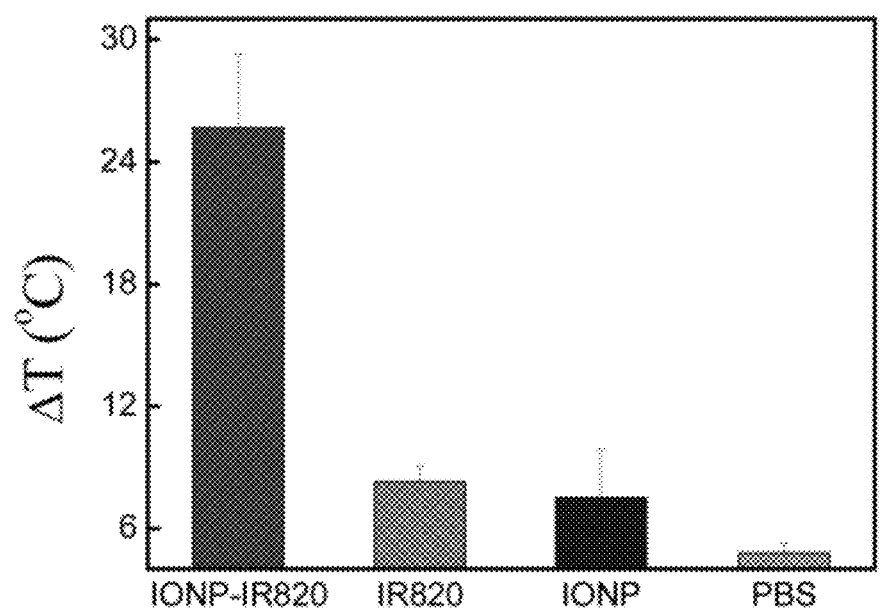
FIG. 28 shows the surface temperature changes of tumors in mice (24 h post intravenously injected with IONP-IR820 and equal amount of free IR820, IONP, and PBS) after laser irradiation for 10 minutes (four mice each group). Error bar is standard deviation. Laser power: 0.5 W.

To quantify the tissue temperature increase during the laser irradiation, an infrared camera (FLIR i7, Boston, Mass.) was used to monitor the surface temperature of mice and tumors. The result of enhanced photothermal effect from IONP-IR820 nanocomposite is shown in FIG. 28. The average temperature increase at the tumor site in mice treated with IONP-IR820 is 25.7±3.6° C. after laser irradiation for 10 minutes (five mice per treatment group). During tumor irradiation, areas of mice which were not exposed to the NIR laser show a negligible temperature increase. In contrast, the surface temperatures of tumors on control treated mice shows the average tumor temperature increase of 8.3±0.8° C. for free IR820, 7.5±2.4° C. for unmodified IONPs, and 4.8±0.5° C. for PBS after laser irradiation with the same laser power and duration of exposure. The average temperature increase for mice injected with IONP-IR820 is ~21° C. higher than that in PBS control group after laser irradiation. It is worth noting the laser power used in this study is 0.5 W, half of the previous laser power. So the tissue temperature increase in PBS control mice is significantly reduced, but the tumor tissues from nano-mediator treated mice ate still able to gain high enough temperature increase comparable to the previous treatment using unmodified IONP with laser power at 1.0 W to kill cancer cells. Previous reports indicate that 1 hour maintenance at 42° C. is necessary to kill cells, with effective exposure time shortening to 3-4 minutes when temperature is increased to 70-80° C. [37]. Dong et al. also reported that a tumor tissue temperature increase to 60° C. is high enough to kill cancer cells after five minutes of laser irradiation for mice intratumorally injected with Fe$_3$O$_4$/Au core/shell nanocomposites [16].

In summary, polysiloxane-containing polymer-coated IONPs were conjugated with IR820 through siloxane chemistry with a density of 2×10$^4$ dye molecules on each nanoparticle. IONPIR820 nanocomposite can significantly enhance the photothermal effect compared to unmodified IONP. IONP-IR820 nanocomposite is able to effectively accumulate to tumor site (9% ID) through intravenous injection to tumor-bearing mice; Enhanced photothermal effect was confirmed in vivo using IONP-IR820 mediator

REFERENCES FOR THIS EXAMPLE

[1] Stewart B W, & Wild, C. P. World Cancer Report. 2014.
[2] De Laurentiis et al. Treatment of triple negative breast cancer (TNBC): current options and future perspectives. Cancer Treat Rev. 2010; 36 Suppl 3:S80-6.
[3] Cherukuri et al., Targeted hyperthermia using metal nanoparticles. Adv Drug Deliver Rev. 2010; 62:339-45.
[4] Yang et al., Nano-graphene in biomedicine: theranostic applications. Chem Soc Rev. 2013; 42:530-47.
[5] Melancon et al., Cancer Theranostics with Near-Infrared Light-Activatable Multimodal Nanoparticles. Accounts Chem Res. 2011; 44:947-56.
[6] Kennedy et al. A New Era for Cancer Treatment: Gold-Nanoparticle-Mediated Thermal Therapies. Small. 2011; 7:169-83.
[7] Ke et al. Gold-Nanoshelled Microcapsules: A Theranostic Agent for Ultrasound Contrast Imaging and Photothermal Therapy. Angew Chem Int Edit. 2011; 50:3017-21.
[8] Hirsch et al. Nanoshell-mediated nearinfrared thermal therapy of tumors under magnetic resonance guidance. P Natl Acad Sci USA. 2003; 100:13549-54.
[9] Kuo et al. Gold Nanorods in Photodynamic Therapy, as Hyperthermia Agents, and in Near-Infrared Optical Imaging. Angew Chem Int Edit. 2010; 49:2711-5.
[10] Huang et al., Cancer cell imaging and photothermal therapy in the near-infrared region by using gold nanorods. Journal of the American Chemical Society. 2006; 128:2115-20.
[11] Yavuz et al. Gold nanocages covered by smart polymers for controlled release with near-infrared light. Nat Mater. 2009; 8:935-9.
[12] Link et al., How does a gold nanorod melt? J Phys Chem B. 2000; 104:7867-70.
[13] Zhou et al., Luminescent gold nanoparticles with efficient renal clearance. Angew Chem Int Ed Engl. 2011; 50:3168-72.
[14] Tian et al. Hydrophilic Flower-Like CuS Superstructures as an Efficient 980 nm Laser-Driven Photothermal Agent for Ablation of Cancer Cells. Adv Mater. 2011; 23:3542-+.
[15] Liu et al., Optimization of surface chemistry on single-walled carbon nanotubes for in vivo photothermal ablation of tumors. Biomaterials. 2011; 32:144-51.
[16] Dong et al. Facile Synthesis of Monodisperse Superparamagnetic Fe3O4 Core@hybrid@Au Shell Nanocomposite for Bimodal Imaging and Photothermal Therapy. Adv Mater. 2011; 23:5392-+.
[17] Ji et al. Bifunctional gold nanoshells with a superparamagnetic iron oxide-silica core suitable for both MR imaging and photothermal therapy. J Phys Chem C. 2007; 111:6245-51.
[18] Zhang et al., Tailored Synthesis of Superparamagnetic Gold Nanoshells with Tunable Optical Properties. Adv Mater. 2010; 22:1905-+.
[19] Fan et al., Multifunctional plasmonic shellmagnetic core nanoparticles for targeted diagnostics, isolation, and photothermal destruction of tumor cells. Acs Nano. 2012; 6:1065-73.
[20] Yue et al. IR-780 dye loaded tumor targeting theranostic nanoparticles for NIR imaging and photothermal therapy. Biomaterials. 2013; 34:6853-61.
[21] Zheng et al., Enhanced Tumor Treatment Using Biofunctional Indocyanine Green-Containing Nanostructure by Intratumoral or Intravenous Injection. Mol Pharmaceut. 2012; 9:514-22.
[22] Fernandez-Fernandez et al. Comparative Study of the Optical and Heat Generation Properties of IR820 and Indocyanine Green. Mol Imaging. 2012; 11:99-113.
[23] Ma et al., Indocyanine green loaded SPIO nanoparticles with phospholipid-PEG coating for dual-modal imaging and photothermal therapy. Biomaterials. 2013; 34:7706-14.
[24] Chen et al. PEGylated Micelle Nanoparticles Encapsulating a Non-Fluorescent Near-Infrared Organic Dye as a Safe and Highly-Effective Photothermal Agent for In Vivo Cancer Therapy. Adv Funct Mater. 2013; 23:5893-902.
[25] Chen et al., Highly crystallized iron oxide nanoparticles as effective and biodegradable mediators for photothermal cancer therapy. J Mater Chem B. 2014; 2:757-65.
[26] Chen et al. Biocompatible Polysiloxane-Containing Diblock Copolymer PEO-b-P gamma MPS for Coating Magnetic Nanoparticles. Acs Appl Mater Inter. 2009; 1:2134-40.
[27] Zheng et al. Indocyanine green-loaded biodegradable tumor targeting nanoprobes for in vitro and in vivo imaging. Biomaterials. 2012; 33:5603-9.
[28] Tang et al., Synthesis and Biological Response of Size-Specific, Monodisperse Drug-Silica Nanoconjugates. Acs Nano. 2012; 6:3954-66.
[29] Strekowski et al., Synthesis of water-soluble nearinfrared cyanine dyes functionalized with [(succinimido)oxy] carbonyl group. J Heterocyclic Chem. 2003; 40:913-6.
[30] Wang et al. Iron Oxide @ Polypyrrole Nanoparticles as a Multifunctional Drug Carrier for Remotely Controlled Cancer Therapy with Synergistic Antitumor Effect. Acs Nano. 2013; 7:6782-95.
[31] Chu et al. Near-infrared laser light mediated cancer therapy by photothermal effect of Fe3O4 magnetic nanoparticles. Biomaterials. 2013; 34:4078-88.
[32] Gu et al. Magnetic-field-assisted photothermal therapy of cancer cells using Fe-doped carbon nanoparticles. J Biomed Opt. 2012; 17.
[33] Cabral et al. Accumulation of sub-100 nm polymeric micelles in poorly permeable tumours depends on size. Nat Nanotechnol. 2011; 6:815-23.
[34] Zhang et al. Influence of anchoring ligands and particle size on the colloidal stability and in vivo biodistribution of polyethylene glycol-coated gold nanoparticles in tumor-xenografted mice. Biomaterials. 2009; 30:1928-36.
[35] Yang et al. Multimodal Imaging Guided Photothermal Therapy using Functionalized Graphene Nanosheets Anchored with Magnetic Nanoparticles. Adv Mater. 2012; 24:1868-72.
[36] Melancon et al. Targeted multifunctional goldbased nanoshells for magnetic resonance-guided laser ablation of head and neck cancer. Biomaterials. 2011; 32:7600-8.
[37] Habash et al. Thermal therapy, part 1: an introduction to thermal therapy. Crit Rev Biomed Eng. 2006; 34:459-89.

REFERENCES

1. Cherukuri P, Glazer E S, Curleya S A: Targeted hyperthermia using metal nanoparticles, Adv Drug Deliver Rev 2010, 62:339-345
2. Melancon M P, Zhou M, Li C: Cancer Theranostics with Near-Infrared Light-Activatable Multimodal Nanoparticles, Accounts Chem Res 2011, 44:947-956
3. Kennedy L C, Bickford L R, Lewinski N A, Coughlin A J, Hu Y, Day E S, West J L, Drezek R A: A New Era for Cancer Treatment: Gold-Nanoparticle-Mediated Thermal Therapies, Small 2011, 7:169-183
4. Yang K, Feng L Z, Shi X Z, Liu Z: Nano-graphene in biomedicine: theranostic applications, Chem Soc Rev 2013, 42:530-547
5. Hirsch L R, Stafford R J, Bankson J A, Sershen S R, Rivera B, Price R E, Hazle J D, Halas N J, West J L: Nanoshell-mediated near-infrared thermal therapy of tumors under magnetic resonance guidance, P Natl Acad Sci USA 2003, 100:13549-13554
6. Ke H T, Wang J R, Dai Z F, Jin Y S, Qu E Z, Xing Z W, Guo C X, Yue X L, Liu J B: Gold-Nanoshelled Microcapsules: A Theranostic Agent for Ultrasound Contrast Imaging and Photothermal Therapy, Angew Chem Int Edit 2011, 50:3017-3021
7. Huang X, El-Sayed I H, Qian W, El-Sayed M A: Cancer cell imaging and photothermal therapy in the near-infrared region by using gold nanorods, J Am Chem Soc 2006, 128:2115-2120
8. Kuo W S, Chang C N, Chang Y T, Yang M H, Chien Y H, Chen S J, Yeh C S: Gold Nanorods in Photodynamic Therapy, as Hyperthermia Agents, and in Near-Infrared Optical Imaging, Angewandte Chemie-International Edition 2010, 49:2711-2715
9. Yavuz M S, Cheng Y Y, Chen J Y, Cobley C M, Zhang Q, Rycenga M, Xie J W, Kim C, Song K H, Schwartz A G, Wang L H V, Xia Y N: Gold nanocages covered by smart polymers for controlled release with near-infrared light, Nat Mater 2009, 8:935-939
10. Chen J Y, Glaus C, Laforest R, Zhang Q, Yang M X, Gidding M, Welch M J, Xia Y N: Gold Nanocages as Photothermal Transducers for Cancer Treatment, Small 2010, 6:811-817
11. http://clinicaltrials.gov/show/nct00848042:
12. http://clinicaltrials.gov/show/nct01679470:
13. http://www.nanospectra.com/clinicians/aurolasetherapy.html:
14. Ji X J, Shao R P, Elliott A M, Stafford R J, Esparza-Coss E, Bankson J A, Liang G, Luo Z P, Park K, Markert J T, Li C: Bifunctional gold nanoshells with a superparamagnetic iron oxide-silica core suitable for both M R imaging and photothermal therapy, J Phys Chem C 2007, 111: 6245-6251
15. Dong W J, Li Y S, Niu D C, Ma Z, Gu J L, Chen Y, Zhao W R, Liu X H, Liu C S, Shi J L: Facile Synthesis of Monodisperse Superparamagnetic Fe3O4 Core@hybrid@Au Shell Nanocomposite for Bimodal Imaging and Photothermal Therapy, Adv Mater 2011, 23:5392-+
16. Yang K, Hu L L, Ma X X, Ye S Q, Cheng L, Shi X Z, Li C H, Li Y G, Liu Z: Multimodal Imaging Guided Photothermal Therapy using Functionalized Graphene Nanosheets Anchored with Magnetic Nanoparticles, Adv Mater 2012, 24:1868-1872
17. Melancon M P, Lu W, Zhong M, Zhou M, Liang G, Elliott A M, Hazle J D, Myers J N, Li C, Stafford R J: Targeted multifunctional gold-based nanoshells for magnetic resonance-guided laser ablation of head and neck cancer, Biomaterials 2011, 32:7600-7608
18. Zhang K, Cutler J I, Zhang J A, Zheng D, Auyeung E, Mirkin C A: Nanopod Formation through Gold Nanoparticle Templated and Catalyzed Cross-linking of Polymers Bearing Pendant Propargyl Ethers, J Am Chem Soc 2010, 132:15151-15153
19. Link S, Wang Z L, El-Sayed M A: How does a gold nanorod melt?, J Phys Chem B 2000, 104:7867-7870
20. Yu W W, Falkner J C, Yavuz C T, Colvin V L: Synthesis of monodisperse iron oxide nanocrystals by thermal decomposition of iron carboxylate salts, Chem Commun 2004, 2306-2307
21. Chen H W, Wu X Y, Duan H W, Wang Y A, Wang L Y, Zhang M M, Mao H: Biocompatible Polysiloxane-Containing Diblock Copolymer PEO-b-P gamma MPS for Coating Magnetic Nanoparticles, Acs Applied Materials & Interfaces 2009, 1:2134-2140
22. Gobin A M, Watkins E M, Quevedo E, Colvin V L, West J L: Near-Infrared-Resonant Gold/Gold Sulfide Nanoparticles as a Photothermal Cancer Therapeutic Agent, Small 2010, 6:745-752
23. Sun X H, Zhang G D, Patel D, Stephens D, Gobin A M: Targeted Cancer Therapy by Immunoconjugated Gold-Gold Sulfide Nanoparticles Using Protein G as a Cofactor, Ann Biomed Eng 2012, 40:2131-2139

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:
1. A composition comprising a plurality of core-satellite nanocomposites, wherein said core-satellite nanocomposites individually comprise:
 a) a core nanoparticle complex comprising a biocompatible coating surrounding a nanoparticle core,
  wherein said biocompatible coating comprises polysiloxane,
  wherein said nanoparticle core comprises $Fe_3O_4$ and has a diameter between 4 and 60 nm, and
 b) a plurality of satellite components attached to, or absorbed to, said biocompatible coating, wherein each of said satellite components comprises a gold, or gold-sulfide, nanoparticle with a diameter between 2 and 5 nm; and
 wherein said plurality of satellite components are visible as discrete nanoparticles, that are not part of a shell surrounding said core nanoparticle complex, using a transmission electron microscope (TEM).
2. The composition of claim 1, further comprising a physiologically compatible aqueous solution.
3. The composition of claim 1, wherein said Fe3O4 is highly crystallized and has an X-ray diffraction (XRD) pattern where the brightest diffraction ring is from the 440 plane.
4. The composition of claim 1, wherein said nanoparticle core has a spherical shape.

5. The composition of claim 1, wherein said nanoparticle core has a cubic shape.

* * * * *